(12) United States Patent
von Aspern et al.

(10) Patent No.: US 9,248,087 B2
(45) Date of Patent: Feb. 2, 2016

(54) ANTI-DANDRUFF HAIR CARE PRODUCTS WITH SELECTIVE ACTIVE INGREDIENTS AND A CATIONIC KERATIN

(71) Applicant: Henkel AG & Co. KGaA, Duesseldorf (DE)

(72) Inventors: Edith von Aspern, Hanstedt (DE); Marcus Krueger, Ellerhoop (DE); Manuela Mette, Kleinfeld (DE); Katharina Bode, Buxtehude (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/063,257

(22) Filed: Oct. 25, 2013

(65) Prior Publication Data
US 2014/0121174 A1    May 1, 2014

(30) Foreign Application Priority Data
Oct. 25, 2012   (DE) .......................... 10 2012 219 588

(51) Int. Cl.
| | | |
|---|---|---|
| *A01N 43/04* | (2006.01) | |
| *A61K 31/70* | (2006.01) | |
| *A61K 8/60* | (2006.01) | |
| *A61Q 5/00* | (2006.01) | |
| *A61K 8/39* | (2006.01) | |
| *A61Q 5/12* | (2006.01) | |
| *A61K 8/86* | (2006.01) | |

(52) U.S. Cl.
CPC ................. *A61K 8/604* (2013.01); *A61K 8/39* (2013.01);*A61K 8/86* (2013.01); *A61Q 5/002* (2013.01); *A61Q 5/004* (2013.01); *A61Q 5/006* (2013.01); *A61Q 5/12* (2013.01)

(58) Field of Classification Search
CPC ........... A61K 8/86; A61K 8/39; A61K 8/604; A61Q 5/004; A61Q 5/002; A61Q 5/006; A61Q 5/12
See application file for complete search history.

(56) References Cited

U.S. PATENT DOCUMENTS

| | | | | |
|---|---|---|---|---|
| 4,102,795 | A * | 7/1978 | Minegishi et al. | 424/70.19 |
| 4,891,045 | A * | 1/1990 | Junino et al. | 8/411 |
| 4,919,846 | A * | 4/1990 | Nakama et al. | 510/433 |
| 5,130,056 | A * | 7/1992 | Jakobson et al. | 510/159 |
| 6,555,515 | B1 * | 4/2003 | Hees et al. | 510/470 |
| 6,838,419 | B2 * | 1/2005 | Pereira et al. | 510/123 |
| 6,953,773 | B2 * | 10/2005 | Pereira et al. | 510/329 |
| 8,420,061 | B2 * | 4/2013 | Satonaka et al. | 424/59 |

FOREIGN PATENT DOCUMENTS

EP    2 366 376 A1 *  9/2011

\* cited by examiner

*Primary Examiner* — Lawrence E Crane
(74) *Attorney, Agent, or Firm* — David K. Benson

(57) ABSTRACT

Hair treatment agents include as care-providing substances selected cationic alkyloligoglucosides in a total quantity from 0.01 to 10.0 wt % that are substituted with linear or branched C6 to C30 alkyl or alkenyl residues, and selected polyglycerol esters in a total quantity from 0.01 to 10.0 wt %, the polyglycerol esters being esters of a fatty acid having 4 to 30 carbon atoms and polyglycerol having 2 to 20 glycerol units.

12 Claims, No Drawings

ANTI-DANDRUFF HAIR CARE PRODUCTS WITH SELECTIVE ACTIVE INGREDIENTS AND A CATIONIC KERATIN

FIELD OF THE INVENTION

The present invention generally relates to hair treatment agents containing selected cationic alkyloligoglucosides and selected polyglycerol esters as care-providing substances.

BACKGROUND OF THE INVENTION

A need exists to further improve hair care products and to impart further advantageous properties to them. In particular, a care-providing complex should be made available that ideally can be used even in conjunction with oxidizing agents and surfactant agents.

Environmental influences and oxidative hair treatments often result in degraded combability properties of the dry and the wet hair. In addition, the shine and moisture balance are disadvantageously influenced by the fact that the external structure of the keratinic fibers has been attacked. A further consequence of repeated treatments of keratinic fibers using surfactant agents and/or oxidizing agents is considerable grease re-absorption by the keratinic fibers, as well as a strong tendency to increased formation of scalp dandruff. In addition, ethoxylated emulsifier agents can become modified as a result of natural UV radiation when they remain on the hair and scalp, and can produce undesirable irritation.

It is therefore an object of the present invention to decrease the side-effects of environmentally related influences and of oxidative as well as surfactant hair treatments, preferably already during the oxidative or surfactant hair treatment but also after the oxidative or surfactant hair treatment, without degrading the efficiency of oxidative or surfactant cosmetic substance, in particular with regard to color intensity, color fidelity, lightening performance and/or waving effect, and to prevent grease re-absorption by the keratinic fibers and increased formation of scalp dandruff. In addition, the oxidative treatment of keratin-containing fibers, in particular human hair, is also to be combined in the form of a 2-in-1 product, in one application step, with the application of effective fiber protection from environmental influences, for example UV protection. The compositions according to the present invention are further intended to be formulated entirely without ethoxylated emulsifier agents.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A hair treatment agent containing, in a cosmetic carrier, based in each case on the total composition: at least one cationic alkyloligoglucoside, in a total quantity from 0.01 to 10.0 wt %, and at least one polyglycerol ester, in a total quantity from 0.01 to 10.0 wt %.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found, surprisingly, that the object can be achieved to an outstanding extent by means of a hair treatment agent that contains an active substance complex containing as essential ingredients at least one cationic alkyloligoglucoside and at least one further quaternary ammonium compound.

Hair treatment agents containing this active substance complex result in improved brightness, improved shine, improved moisture balance, and protection from oxidative damage, and in prevention of grease re-absorption by the keratinic fibers and in an increase in the washing fastness of colored keratinic fibers, in particular of human hair, and in a time delay in the formation of dandruff.

"Hair treatment agents" for purposes of the present invention are, for example, hair shampoos, hair conditioners, conditioning shampoos, hair rinses, hair treatments, hair packs, hair tonics, hair coloring shampoos, or combinations thereof. Compositions that condition the hair, such as hair rinses, hair treatments, hair packs, hair oils and lotions, both as leave-on products, i.e. ones that remain on the hair until the hair is next washed, and as rinse-off products, i.e. products to be rinsed off again a few seconds to a few hours after utilization, are to be understood in particular as hair treatment agents according to the present invention. Formulations that remain on the hair as leave-on products are preferred according to the present invention. Compositions according to the present invention that are utilized as a spray are particularly preferred. Non-aerosol applications are in turn highly preferred. Most highly preferably of all, the formulations according to the present invention are clear, leave-on, non-aerosol sprays.

"Combability" is understood according to the present invention as both the combability of the wet fibers and the combability of the dry fibers.

"Softness" is defined as the tactility of an assemblage of fibers, in which context one skilled in the art sensorially feels and evaluates the "fullness" and "suppleness" parameters of the assemblage.

"Shapability" is understood as the ability to impart a change in shape to an assemblage of previously treated keratin-containing fibers, in particular human hairs. The term "stylability" is also used in hair cosmetics.

"Restructuring" is to be understood for purposes of the invention as a reduction in the damage to keratinic fibers resulting from a wide variety of influences. Restoration of natural strength plays an essential role here, for example. Restructured fibers are notable for improved shine, improved softness, and easier combability. In addition, they exhibit improved strength and elasticity. Successful restructuring can moreover be demonstrated physically as an increase in melting point as compared with the damaged fiber. The higher the melting point of the hair, the stronger the structure of the fiber.

"Washing fastness" is to be understood for purposes of the invention as maintenance of the original coloring, in terms of shade and/or intensity, when the keratinic fiber is exposed to the repeated influence of aqueous agents, in particular surfactant-containing agents such as shampoos.

The compositions according to the present invention containing the active substance complex according to the present invention are further notable for an appreciably improved state of the keratinic fibers in terms of the moisture balance of the keratinic fibers. The active substance complex according to the present invention furthermore results in appreciable protection of the keratinic fibers from heat effects, for example when blow-drying keratinic fibers. Protection of the surface of keratinic fibers from heat effects is of great importance in particular when irons or hair driers are used. Lastly, it has been found, surprisingly, that the compositions according to the present invention result in appreciably delayed re-soiling of the keratinic fibers. In addition, the formation of dandruff on the scalp is appreciably delayed. Lastly, the dermatological compatibility of the compositions according to the present invention is considerably improved.

outstanding combability of both wet and dry hair. In addition, these compositions according to the present invention exhibit outstanding volume values for the completely styled hairstyle.

The first obligatory component is a cationic alkyloligoglucoside as shown in the following illustration:

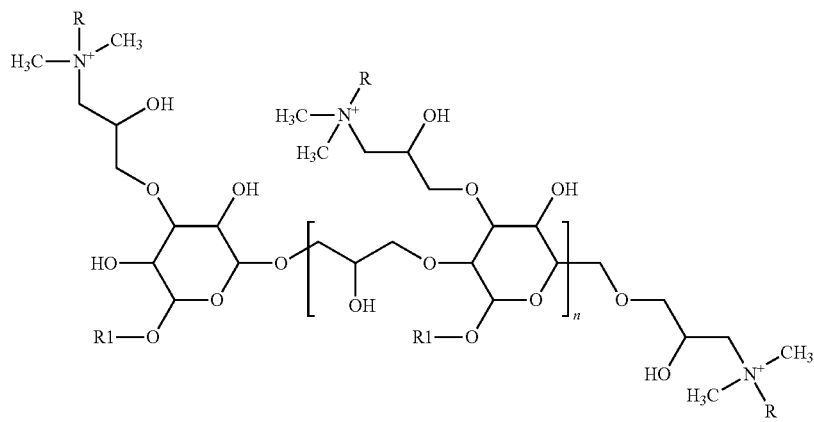

An aqueous cosmetic carrier contains at least 50 wt % water.

"Aqueous alcoholic" cosmetic carriers are to be understood for purposes of the present invention as aqueous solutions containing 3 to 70 wt % of a $C_1$ to $C_6$ alcohol, in particular methanol, ethanol, propanol, isopropanol, butanol, isobutanol, tert-butanol, n-pentanol, isopentanols, n-hexanol, isohexanols, glycol, glycerol, 1,2-pentanediol, 1,5-pentanediol, 1,2-hexanediol, or 1,6-hexanediol. The agents according to the present invention can additionally contain further organic solvents such as, for example, methoxybutanol, benzyl alcohol, ethyl diglycol, or 1,2-propylene glycol. All water-soluble organic solvents are preferred in this context. Water is particularly preferred.

A first subject of the present invention is therefore a hair treatment agent containing, in a suitable cosmetic carrier, based in each case on the total composition of the agent:
a) at least one cationic alkyloligoglucoside, in a total quantity from 0.01 to 10.0 wt %,
b) at least one polyglycerol ester, in a total quantity from 0.01 to 10.0 wt %.

The use of this combination results in surprisingly good properties in the treated hair, in particular improved combability properties, improved shine, and improved elasticity, as well as appreciably increased washing fastness of colored hair, and in longer durability simultaneously with better reshaping performance in the context of waving operations such as water waving and permanent waving. This is even more surprising given that it is possible with these active substance combinations at least to reduce the concentration of fatty alcohols in conditioning compositions. The term "fatty alcohol" is known to one skilled in the art, but will be described in detail at a later juncture. A "fatty alcohol" is understood in the present compound as a linear, branched, saturated, or unsaturated alcohol having at least 10 to 30 carbon atoms. The concentration of fatty alcohols can be limited to quantities less than 2.0 wt %, particularly preferably in fact to quantities less than 1.0 wt % and highly preferably to quantities less than 0.5 wt %. The great advantage of a reduction in the fatty alcohol content is considerably decreased stress on the keratinic fibers, simultaneously with In the formula depicted above, residues R mutually independently denote a linear or branched C6 to C30 alkyl residue, a linear or branched C6 to C30 alkenyl residue; by preference residue R denotes a residue R selected from lauryl, myristyl, cetyl, stearyl, oleyl, behenyl, or arachidyl.

Residues R1 mutually independently denote a linear or branched C6 to C30 alkyl residue, a linear or branched C6 to C30 alkenyl residue; by preference residue R denotes a residue selected from butyl, capryl, caprylyl, octyl, nonyl, decanyl, lauryl, myristyl, cetyl, stearyl, oleyl, behenyl, or arachidyl. Particularly preferably, residues R1 are identical. Even more preferably, residues R1 are selected from industrial mixtures of the fatty alcohol cuts from C6/C8 fatty alcohols, C8/C10 fatty alcohols, C10/C12 fatty alcohols, C12/C14 fatty alcohols, C12/C18 fatty alcohols, and highly preferably these are those industrial fatty alcohol cuts that are of vegetable origin.

Particularly preferred examples of cationic alkyloligoglucosides are the compounds having the International Nomenclature of Cosmetic Ingredients (INCI) names Polyquaternium-77, Polyquaternium-78, Polyquaternium-79, Polyquaternium-80, Polyquaternium-81, and Polyquaternium-82. The cationic alkyloligoglucosides having the names Polyquaternium-77, Polyquaternium-81, and Polyquaternium-82 are highly preferred.

Compounds of this kind can be acquired, for example, from Colonial Chemical Inc. under the name Poly Suga® Quat.

The cationic alkyloligoglucosides are used in a total quantity from 0.01 to 10.0 wt %, by preference from 0.05 to 5.0 wt %, even more preferably from 0.1 to 3.0 wt %, and highly preferably in quantities from 0.2 to 2.0 wt %, based in each case on the total weight of the composition. Also encompassed according to the present invention is of course the fact that more mixtures of cationic alkyloligoglucosides can be used. It is preferred in this case if one long-chain and one short-chain cationic alkyloligoglucoside are used simultaneously in each case.

The second obligatory component of the active substance complex according to the present invention is a polyglycerol ester. Polyglycerol esters are esters of a fatty acid and polyglycerol. Polyglycerol is made up of 2 to 20 glycerol units.

Polyglycerol esters having 2, 3, 4, 5, 6, 7, 8, 9, 10, 12, 14, 16, 18, or 20 glycerol units per molecule of polyglycerol esters are preferred. Polyglycerol esters having 2, 4, 6, 8, or 10 glycerol units per molecule of polyglycol ester are particularly preferred. Polyglycerol esters having 2, 4, or 6 glycerol units in the molecule are highly preferred. The fatty acid residues of the polyglycerol esters are linear and/or branched, saturated and/or unsaturated fatty acids having 4 to 30 carbon atoms. Fatty acids having 4 to 22 carbon atoms are preferred. To be recited among these are, for example, isostearic acid and isopalmitic acid. Further typical examples of such fatty acids are succinic acid, sebacic acid, caproic acid, caprylic acid, 2-ethylhexanoic acid, capric acid, lauric acid, isotridecanoic acid, myristic acid, palmitic acid, palmitoleic acid, stearic acid, oleic acid, elaidic acid, petroselinic acid, linoleic acid, linolenic acid, eleostearic acid, arachidonic acid, gadoleic acid, behenic acid, and erucic acid, as well as mixtures of these fatty acids. The fatty acid residues of the polyglyceryl esters are preferably selected from sebacic acid, caproic acid, caprylic acid, 2-ethylhexanoic acid, capric acid, lauric acid, myristic acid, palmitic acid, oleic acid, elaidic acid, linoleic acid, behenic acid, and erucic acid, as well as mixtures of these fatty acids. Preferred mixtures of fatty acids are mixtures of at least, in each case, sebacic acid and lauric acid, caproic acid and caprylic acid. Polyglycerol esters in which the polyglycerol contains 2, 4, 6, or 8 glycerol units per molecule and the fatty acid component is a mixture of sebacic acid and lauric acid and/or a mixture of caproic acid and caprylic acid, are highly preferred. Only one, two, three, four, five, six, seven, eight, nine, ten, or at most all of the OH groups of the polyglycerol can be esterified with the fatty acids. Mono-, di-, tri-, tetra-, or pentaesters are preferred. The diesters are highly preferred. Diesters in which the underlying polyglycerol is esterified with two different fatty acids are most highly preferred.

Examples of such compounds are obtainable commercially under the INCI names Polyglyceryl-4 Caprate, Polyglyceryl-2 Caprate, Polyglyceryl-4 Caprylate, Polyglyceryl-6 Caprylate, Polyglyceryl-6 Caprate, Polyglyceryl-4 Caprylate/Caprate, Polyglyceryl-6 Caprylate/Caprate, Polyglyceryl-3 Cocoate, Polyglyceryl-4 Cocoate, Polyglyceryl-10 Decalinoleate, Polyglyceryl-10 Decaoleate, Polyglyceryl-10 Decacasterate, Polyglyceryl-3 Dicaprate, Polyglyceryl-3 Dicocoate, Polyglyceryl-10 Didecanoate, Polyglyceryl-2 Diisostearate, Polyglyceryl-3 Diisostearate, Polyglyceryl-10 Diisostearate, Polyglyceryl-4 Dilaurate, Polyglycerin-2 Dioleate, Polyglyceryl-3 Dioleate, Polyglyceryl-6 Dioleate, Polyglyceryl-10 Dioleate, Polyglyceryl-6 Dipalmitate, Polyglyceryl-10 Dipalmitate, Polyglyceryl-2 Dipolyhydroxystearate, Polyglyceryl-2 Distearate, Polyglyceryl-3 Distearate, Polyglyceryl-6 Distearate, Polyglyceryl-10 Distearate, Polyglyceryl-10 Heptaoleate, Polyglyceryl-10 Heptastearate, Polyglyceryl-6 Hexaoleate, Polyglyceryl-10 Hexaoleate, Polyglyceryl-2 Isopalmitate, Polyglyceryl-2 Isostearate, Polyglyceryl-4 Isostearate, Polyglyceryl-5 Isostearate, Polyglyceryl-6 Isostearate, Polyglyceryl-10 Isostearate, Polyglyceryl-2 Laurate, Polyglyceryl-3 Laurate, Polyglyceryl-4 Laurate, Polyglyceryl-4 Laurate/Sebacate, Polyglyceryl-4 Laurate/Succinate, Polyglyceryl-5 Laurate, Polyglyceryl-6 Laurate, Polyglyceryl-10 Laurate, Polyglyceryl-3 Myristate, Polyglyceryl-10 Myristate, Polyglyceryl-2 Oleate, Polyglyceryl-3 Oleate, Polyglyceryl-4 Oleate, Polyglyceryl-5 Oleate, Polyglyceryl-6 Oleate, Polyglyceryl-8 Oleate, Polyglyceryl-10 Oleate, Polyglyceryl-3 Palmitate, Polyglyceryl-6 Palmitate, Polyglyceryl-10 Palmitate, Polyglyceryl-10 Pentalaurate, Polyglyceryl-10 Pentalinoleate, Polyglyceryl-4 Pentaoleate, Polyglyceryl-10 Pentaoleate, Polyglyceryl-3 Pentaricinoleate, Polyglyceryl-6 Pentaricinoleate, Polyglyceryl-10 Pentaricinoleate, Polyglyceryl-4 Pentastearate, Polyglyceryl-6 Pentastearate, Polyglyceryl-10 Pentastearate, Polyglyceryl-3 Polyrisinoleate, Polyglyceryl-6 Polyricinoleate, Polyglyceryl-3 Ricinoleate, Polyglyceryl-2 Sesquiisostearate, Polyglyceryl-2 Sesquioleate, Polyglyceryl-2 Sesquistearate, Polyglyceryl-3 Stearate, Polyglyceryl-2 Stearate, Polyglyceryl-4 Stearate, Polyglyceryl-8 Stearate, Polyglyceryl-10 Stearate, Polyglyceryl-2 Tetraisostearate, Polyglyceryl-6 Tetraoleate, Polyglyceryl-10 Tetraoleate, Polyglyceryl-2 Tetrastearate, Polyglyceryl-2 Triisostearate, Polyglyceryl-3 Triisostearate, Polyglyceryl-10 Trioleate, Polyglyceryl-4 Tristearate, Polyglyceryl Tristearate, Polyglyceryl-10 Tristearate.

Polyglyceryl-4 Caprate, Polyglyceryl-2 Caprate, Polyglyceryl-4 Caprylat, Polyglyceryl-6 Caprylat, Polyglyceryl-6 Caprate, Polyglyceryl-4 Caprylate/Caprate, Polyglyceryl-6 Caprylate/Caprate, Polyglyceryl-3 Cocoate, Polyglyceryl-4 Cocoate, Polyglyceryl-2 Laurate, Polyglyceryl-3 Laurate, Polyglyceryl-4 Laurate, Polyglyceryl-4 Laurate/Sebacate, Polyglyceryl-4 Laurate/Succinate, Polyglyceryl-5 Laurate, Polyglyceryl-6 Laurate, Polyglyceryl-10 Laurate, and mixtures thereof are used with particular preference.

Such products are obtainable, for example, under the trade names Dehymuls® PGPH (BASF) or NatraGem® (Croda).

Polyglycerol esters are used in a quantity from 0.01 to 10 wt %, preferably from 0.01 to 7.0 wt %, more preferably from 0.01 to 5.0 wt %, with further preference from 0.05 to 5.0 wt %, and highly preferably from 0.1 to 5.0 wt %.

A further highly preferred component of the active substance complex is at least one quaternary ammonium compound, in a total quantity from 0.1 to 10.0 wt %, selected from at least one of the groups of
  esterquats; and/or
  quaternary imidazolines of formula I,

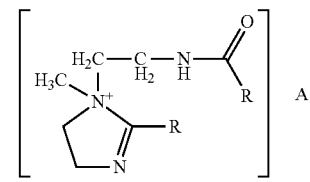

formula I in which residues R, mutually independently in each case, denote a saturated or unsaturated, linear or branched hydrocarbon residue having a chain length from 8 to 30 carbon atoms, and A denotes a physiologically acceptable anion; and/or
cetrimonium chloride and/or behentrimonium chloride; and/or
amines and/or cationized amines; and/or
poly(methacryloyloxyethyltrimethylammonium) compounds; and/or
quaternized cellulose derivatives, in particular Polyquaternium-10 and/or Polyquaternium-24 and/or Polyquaternium-67 and/or Polyquaternium-72; and/or
cationized honey; and/or
cationic guar derivatives; and/or
chitosan; and/or
polymeric dimethyldiallylammonium salts and copolymers thereof with esters and amides of acrylic acid and methacrylic acid; and/or copolymers of vinylpyrrolidone with quaternized derivatives of dialkylaminoalkyl acrylate and methacrylate; and/or vinylpyrrolidone-vinylimidazolium methochloride copolymers; and/or quaternized polyvinyl alcohol; and/or Polyquaternium-2; and/or Polyquaternium-7; and/or Polyquaternium-16; and/or Polyquaternium-17; and/or Polyquaternium-18; and/or Polyquaternium-27; and/or Polyquaternium-69; and/or Polyquaternium-74.

Esterquats in accordance with formula (Tkat1-2) are the first group of the quaternary ammonium compounds.

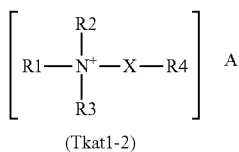

(Tkat1-2)

Residues R1, R2, and R3 therein are each mutually independent and can be identical or different. Residues R1, R2, and R3 signify:
  a branched or unbranched alkyl residue having 1 to 4 carbon atoms, which can contain at least one hydroxyl group, or
  a saturated or unsaturated, branched or unbranched, or cyclic saturated or unsaturated alkyl residue having 6 to 30 carbon atoms, which can contain at least one hydroxyl group, or
  an aryl or alkaryl residue, for example phenyl or benzyl, the residue (—X—R4), provided that at most two of the residues R1, R2, or R3 can denote this residue.

The residue —(X—R4) is included at least 1 to 3 times.

In this, X denotes:
1) —(CH$_2$)$_n$—, where n=1 to 20, by preference n=1 to 10, and particularly preferably n=1 to 5, or
2) —(CH$_2$—CHR$_5$—O)n-, where n=1 to 200, by preference 1 to 100, particularly preferably 1 to 50, and particularly preferably 1 to 20, where R5 has the meaning of hydrogen, methyl, or ethyl,
3) a hydroxyalkyl group having one to four carbon atoms, which can be branched or unbranched and which contains at least one and at most 3 hydroxy groups. Examples of —X are: CHOH, —CHCH$_2$OH, —CH$_2$CHOH, —COHCHOH, —CHOHCOH, —CHCHOHCH$_3$, —CH$_2$COHCH$_3$, —CH$_2$CHOHCH$_2$, —C(CH$_2$OH)$_2$, —CH$_2$CHOHCH$_2$OH, —CH$_2$CH$_2$CHOH, —CH$_2$COHCH$_3$, and hydroxybutyl residues, where the bond from —X to R4 proceeds from the free valence of the relevant carbon atom, and R4 denotes:
1) R6—O—CO—, in which R6 is a saturated or unsaturated, branched or unbranched, or a cyclic saturated or unsaturated alkyl residue having 6 to 30 carbon atoms, which can contain at least one hydroxy group, and which optionally can be further oxyethylated with 1 to 100 ethylene oxide units and/or 1 to 100 propylene oxide units, or
2) R7—CO—, in which R7 is a saturated or unsaturated, branched or unbranched, or a cyclic saturated or unsaturated alkyl residue having 6 to 30 carbon atoms, which can contain at least one hydroxy group, and which optionally can be further oxyethylated with 1 to 100 ethylene oxide units and/or 1 to 100 propylene oxide units, and A denotes a physiologically acceptable organic or inorganic anion and is defined at this juncture representatively for all structures including those described hereinafter. The anion of all cationic compounds described is selected from the halide ions, fluoride, chloride, bromide, iodide, sulfates of the general formula $RSO_3^-$, in which R has the meaning of a saturated or unsaturated alkyl residue having 1 to 4 carbon atoms, or anionic residues of organic acids such as maleate, fumarate, oxalate, tartrate, citrate, lactate, or acetate.

Such products are marketed, for example, under the trademarks Rewoquat®, Stepantex®, Dehyquart®, Armocare®, and Akypoquat®. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90, and Akypoquat® 131 are examples of these esterquats.

Further compounds of formula (Tkat1-2) that are particularly preferred according to the present invention conform to formula (Tkat1-2.1), the cationic betaine esters

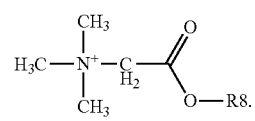

(Tkat1-2.1)

The meaning of R8 corresponds to that of R7.

The esterquats having the commercial names Armocare® VGH-70 as well as Dehyquart® F-75, Dehyquart® L80, Stepantex® VS 90, and Akypoquat® 131 are particularly preferred.

Quaternary imidazoline compounds are a further group. Formula (Tkat2) depicted below shows the structure of these compounds:

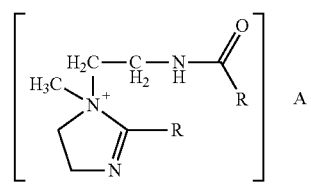

(Tkat2)

Residues R denote, mutually independently in each case, a saturated or unsaturated, linear or branched hydrocarbon residue having a chain length from 8 to 30 carbon atoms. The preferred compounds of formula (Tkat2) each contain the same hydrocarbon residue for R. The chain length of residues R is preferably 12 to 21 carbon atoms. "A" denotes an anion as described above. Examples that are particularly in accordance with the present invention are obtainable, for example, under the INCI names Quaternium-27, Quaternium-72, Quaternium-83, and Quaternium-91. Quaternium-91 is highly preferred according to the present invention.

Cationic surfactants of formula (Tkat-1) are the third group of preferred quaternary ammonium compounds.

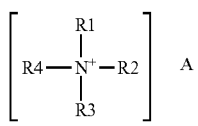 (Tkat1)

In formula (Tkat1), R1, R2, R3, and R4, mutually independently in each case, denote hydrogen, a methyl group, a phenyl group, a benzyl group, a saturated, branched or unbranched alkyl residue having a chain length from 8 to 30 carbon atoms, which optionally can be substituted with one or more hydroxy groups. "A" denotes a physiologically acceptable anion, for example halides such as chloride or bromide, as well as methosulfates.

Examples of compounds of formula (Tkat1) are lauryltrimethylammonium chloride, cetyltrimethylammonium chloride, cetyltrimethylammonium bromide, cetyltrimethylammonium methosulfate, dicetyldimethylammonium chloride, tricetylmethylammonium chloride, stearyltrimethylammonium chloride, distearyldimethylammonium chloride, lauryldimethylbenzylammonium chloride, behenyltrimethylammonium chloride, behenyltrimethylammonium bromide, behenyltrimethylammonium methosulfate. Compounds having at least one cetyl or behenyl residue in the molecule are particularly preferred. Cetyltrimethylammonium and behenyltrimethylammonium salts are highly preferred; cetyltrimethylammonium chloride and behenyltrimethylammonium chloride are most highly preferred.

Amines and/or cationized amines, in particular amidoamines and/or cationized amidoamines, are the last group of quaternary ammonium compounds. In a particularly preferred embodiment of the invention the agents according to the present invention contain, besides at least one further one of the quaternary ammonium compounds, at least one amine and/or cationized amine, in particular an amidoamine and/or a cationized amidoamine, having the following structural formulas:

R1-NH—(CH₂)ₙ—N⁺R²R³R⁴A (Tkat3), in which R1 signifies an acyl or alkyl residue having 6 to 30 carbon atoms which can be branched or unbranched, saturated or unsaturated, and such that the acyl residue and/or the alkyl residue can contain at least one OH group, and
$R^2$, $R^3$, and $R^4$, mutually independently in each case, signify
1) hydrogen, or
2) an alkyl residue having 1 to 4 carbon atoms, which can be identical or different, saturated or unsaturated, and
3) a branched or unbranched hydroxyalkyl group having one to 4 carbon atoms, having at least one and at most three hydroxy groups, for example —CH₂OH, —CH₂CH₂OH, —CHOHCHOH, —CH₂CHOHCH₃, —CH(CH₂OH)₂, —COH(CH₂OH)₂, —CH₂CHOHCH₂OH, —CH₂CH₂CH₂OH, and hydroxybutyl residues, and
A signifies an anion as described above, and
n signifies an integer between 1 and 10.

A composition in which the amine and/or the quaternized amine according to the general formulas (Tkat3) is an amidoamine and/or a quaternized amidoamine, in which R1 signifies a branched or unbranched, saturated or unsaturated acyl residue having 6 to 30 carbon atoms, which can contain at least one OH group, is preferred. A fatty acid residue made of oils and waxes, in particular natural oils and waxes, is preferred here. Suitable examples thereof are lanolin, beeswax, or candelilla wax.

Also preferred are those amidoamines and/or quaternized amidoamines in which $R^2$, $R^3$, and/or $R^4$ in formula (Tkat3) signify a residue according to the general formula CH₂CH₂OR5, in which R5 can have the meaning of alkyl residues having 1 to 4 carbon atoms, hydroxyethyl, or hydrogen. The preferred value of n in the general formula (Tkat8) is an integer between 2 and 5.

The alkylamidoamines both can be present as such, and can be converted by protonation in a correspondingly acid solution into a quaternary compound in the composition. The cationic alkylamidoamines are preferred according to the present invention.

Examples of commercial products of this kind according to the present invention are Witcamine® 100, Incromine® BB, Mackine® 401 and other Mackine grades, Adogen® S18V and, as permanently cationic aminoamines: Rewoquat® RTM 50, Empigen® CSC, Swanol® Lanoquat DES-50, Rewoquat® UTM 50, Schercoquat® BAS, Lexquat® AMG-BEO, or Incroquat® Behenyl HE.

All the quaternary ammonium compounds recited above are cationic surfactants and can be used individually or in any desired combinations with one another, quantities between 0.01 and 10 wt %, preferably quantities from 0.01 to 7.5 wt %, and very particularly preferably quantities from 0.1 to 5.0 wt % being contained. The best results of all are obtained with quantities from 0.1 to 3.0 wt %, based in each case on the total composition of the respective agent. These quantities do not exceed or fall below these values even when mixtures of the cationic surfactants are used.

Besides the cationic surfactants, polymeric compounds are also to be included among the quaternary ammonium compounds. From the large number of these possible ingredients, the classes of cationic and/or amphoteric polymers, described below, are preferred.

The cationic and/or amphoteric polymers can be homo- or copolymers or polymers based on natural polymers, the quaternary nitrogen groups being contained either in the polymer chain or, by preference, as a substituent on one or more of the monomers. The ammonium-group-containing monomers can be copolymerized with non-cationic monomers. Suitable cationic monomers are unsaturated, radically polymerizable compounds that carry at least one cationic group, in particular ammonium-substituted vinyl monomers such as, for example, trialkylmethacryloxyalkylammonium, trialkylacryloxyalkylammonium, dialkyldiallylammonium, and quaternary vinylammonium monomers having cyclic groups containing cationic nitrogens, such as pyridinium, imidazolium, or quaternary pyrrolidones, e.g. alkylvinylimidazolium, alkylvinylpyridinium, or alkylvinylpyrrolidone salts. The alkyl groups of these monomers are by preference lower alkyl groups such as, for example, C1 to C7 alkyl groups, particularly preferably C1 to C3 alkyl groups.

The ammonium-group-containing monomers can be copolymerized with non-cationic monomers. Suitable comonomers are, for example, acrylamide, methacrylamide; alkyl and dialkyl acrylamide, alkyl and dialkyl methacrylamide, alkyl acrylate, alkyl methacrylate, vinylcaprolactone, vinylcaprolactam, vinylpyrrolidone, vinyl esters, e.g. vinyl acetate, vinyl alcohol, propylene glycol, or ethylene glycol, the alkyl groups of these monomers being by preference C1 to C7 alkyl groups, particularly preferably C1 to C3 alkyl groups.

A highly preferred polymer is obtainable commercially under the name Polyquaternium-74.

A particularly suitable homopolymer is the poly(methacryloyloxyethyltrimethylammonium) chloride (crosslinked, if desired) having the INCI name Polyquaternium-37. Such products are available commercially, for example, under the designations Rheocare® CTH (Cosmetic Rheologies) and Synthalen® CR (3V Sigma).

The homopolymer is used preferably in the form of a nonaqueous polymer dispersion. Polymer dispersions of this kind are obtainable commercially under the names Salcare® SC 95 and Salcare® SC 96.

A further very particularly preferred cationic polymer according to the present invention is the copolymer of N-vinylpyrrolidone, N-vinylcaprolactam, N-(3-dimethylaminopropyl)methacrylamide, and 3-(methacryloylamino)propyllauryldimethylammonium chloride (INCI name: Polyquaternium-69) that is marketed, for example, by the ISP company under the commercial name Aquastyle® 300 (28 to 32 wt % active substance in ethanol/water mixture, molecular weight 350,000).

Suitable cationic polymers that are derived from natural polymers are cationic derivatives of polysaccharides, for example cationic derivatives of cellulose, starch, or guar. Chitosan and chitosan derivatives are also suitable. Cationic polysaccharides have the general formula -G-O—B—N$^+$ R$_a$R$_b$R$_c$ A$^-$ G is an anhydroglucose residue, for example starch anhydroglucose or cellulose anhydroglucose;

B is a divalent connecting group, for example alkylene, oxyalkylene, polyoxyalkylene, or hydroxyalkylene;

R$_a$, R$_b$ and R$_c$ mutually independently are alkyl, aryl, alkylaryl, arylalkyl, alkoxyalkyl, or alkoxyaryl each having up to 18 carbon atoms, the total number of carbon atoms in R$_a$, R$_b$, and R$_c$ by preference being a maximum of 20, A$^-$ is a usual counter anion and is by preference chloride.

Cationic (i.e. quaternized) celluloses are obtainable on the market with different degrees of substitution, cationic charge density, nitrogen contents, and molecular weights. For example, Polyquaternium-67 is offered commercially under the names Polymer® SL or Polymer® SK (Amerchol). A further highly preferred cellulose is offered by the Croda company under the commercial name Mirustyle® CP. This is a Trimonium and Cocodimonium Hydroxyethylcellulose, constituting a derivatized cellulose, having the INCI-name Polyquaternium-72. Polyquaternium-72 can be used both in solid form and already predissolved in aqueous solution.

Further cationic celluloses are available under the names Polymer JR® 400 (Amerchol, INCI name Polyquaternium-10) and Polymer Quatrisoft® LM-200 (Amerchol, INCI name Polyquaternium-24). Further commercial products are the compounds Celquat® H 100 and Celquat® L 200. Particularly preferred cationic celluloses are Polyquaternium-24, Polyquaternium-67, and Polyquaternium-72.

Suitable cationic guar derivatives are marketed under the commercial designation Jaguar® and have the INCI name Guar Hydroxypropyltrimonium Chloride. Particularly suitable cationic guar derivatives are additionally available commercially from the Hercules company under the designation N-Hance®. Further cationic guar derivatives are marketed by the Cognis company under the designation Cosmedia®. A preferred cationic guar derivative is the commercial product AquaCat® of the Hercules company. This raw material is a cationic guar derivative that is already predissolved. The cationic guar derivatives are preferred according to the present invention.

A suitable chitosan is marketed, for example, by the Kyowa Oil & Fat company, Japan, under the trade name Flonac®. A preferred chitosan salt is chitosonium pyrrolidonecarboxylate, which is marketed e.g. under the designation Kytamerr® PC by the Amerchol company, USA. Further chitosan derivatives are readily available commercially under the commercial designations Hydagen® CMF, Hydagen® HCMF, and Chitolam® NB/101.

Further preferred cationic polymers are, for example:

cationized honey, for example the commercial product Honeyquat® 50, polymeric dimethyldiallylammonium salts and copolymers thereof with esters and amides of acrylic acid and methacrylic acid. The products obtainable commercially under the designations Merquat® 100 (poly(dimethyldiallylammonium chloride)) and Merquat® 550 (dimethyldiallylammonium chloride/acrylamide copolymer) are examples of such cationic polymers, having the INCI name Polyquaternium-7, vinylpyrrolidone/vinylimidazolium methochloride copolymers, such as those offered under the designations Luviquat® FC 370, FC 550, and the INCI name Polyquaternium-16, as well as FC 905 and HM 552, quaternized vinylpyrrolidone/dimethylaminoethyl methacrylate, for example vinylpyrrolidone/dimethylaminoethyl methacrylate methosulfate copolymer that is marketed under the commercial names Gafquat® 755 N and Gafquat® 734 by the GAF company, USA, and the INCI name Polyquaternium-11, quaternized poly(vinylalcohol), and the polymers known under the names Polyquaternium-2, Polyquaternium-17, Polyquaternium-18, and Polyquaternium-27, having quaternary nitrogen atoms in the main polymer chain, vinylpyrrolidone/vinylcaprolactam/acrylate terpolymers such as those having acrylic acid esters and acrylic acid amides as a third monomer module, and offered commercially e.g. under the designation Aquaflex® SF 40.

Amphoteric polymers used with very particular preference according to the present invention are copolymerizates of diallyldimethylammonium chloride and acrylic acid. These copolymerizates are marketed under the INCI name Polyquaternium-22, inter alia with the commercial name Merquat® 280 (Nalco).

Amphoteric polymers based on a comonomer and used with very particular preference according to the present invention are terpolymers of diallyldimethylammonium chloride, acrylamide, and acrylic acid. These copolymerizates are marketed under the INCI name Polyquaternium-39, inter alia with the commercial name Merquat® Plus 3330 (Nalco).

Amphoteric polymers can in general be used according to the present invention both directly and in a salt form that is obtained by neutralizing the polymerizate, for example using an alkali hydroxide.

The polymers described so far represent only some of the polymers usable according to the present invention. To eliminate the need describe all cationic and/or amphoteric polymers suitable according to the present invention, as well as their composition, the INCI declarations of the polymers preferred according to the present invention will indicated in summary fashion. The polymers preferred according to the present invention carry the INCI names: Polyquaternium-28, Polyquaternium-32, Polyquaternium-33, Polyquaternium-34, Polyquaternium-35, Polyquaternium-41, Polyquaternium-42, Polyquaternium-44, Polyquaternium-47, Polyquaternium-55, Polyquaternium-67, Polyquaternium-68, Polyquaternium-69, Polyquaternium-72, Polyquaternium-74, Polyquaternium-76, Polyquaternium-86, Polyquaternium-89 and Polyquaternium-95, and mixtures thereof.

The cationic polymers recited above can be used individually or in any combinations with one another, quantities between 0.01 and 10 wt %, preferably quantities from 0.01 to 7.5 wt %, and very particularly quantities from 0.1 to 5.0 wt % being contained. The best results of all are obtained with quantities from 0.1 to 3.0 wt %, based in each case on the total composition of the respective agent.

A second subject of the present invention is therefore a hair treatment agent containing:
a) at least one cationic alkyloligoglucoside, in a total quantity from 0.01 to 10.0 wt %,
b) at least one polyglycerol ester, in a total quantity from 0.01 to 10.0 wt %, and at least one quaternary ammonium compound, in a total quantity from 0.1 to 10.0 wt %, selected from at least one of the groups of
esterquats; and/or
quaternary imidazolines of formula I,

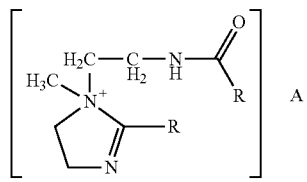

in which residues R, mutually independently in each case, denote a saturated or unsaturated, linear or branched hydrocarbon residue having a chain length from 8 to 30 carbon atoms, and A denotes a physiologically acceptable anion; and/or
cetrimonium chloride and/or behentrimonium chloride; and/or
amines and/or cationized amines; and/or
poly(methacryloyloxyethyltrimethylammonium) compounds; and/or
quaternized cellulose derivatives, in particular Polyquaternium-10 and/or Polyquaternium-24 and/or Polyquaternium-67 and/or Polyquaternium-72; and/or
cationized honey; and/or
cationic guar derivatives; and/or
chitosan; and/or
polymeric dimethyldiallylammonium salts and copolymers thereof with esters and amides of acrylic acid and methacrylic acid; and/or
copolymers of vinylpyrrolidone with quaternized derivatives of dialkylaminoalkyl acrylate and methacrylate; and/or
vinylpyrrolidone-vinylimidazolium methochloride copolymers; and/or
quaternized polyvinyl alcohol; and/or
Polyquaternium-2; and/or
Polyquaternium-7; and/or
Polyquaternium-16; and/or
Polyquaternium-17; and/or
Polyquaternium-18; and/or
Polyquaternium-27; and/or
Polyquaternium-69; and/or
Polyquaternium-74.

It is furthermore highly preferred according to the present invention if at least one amphoteric and/or zwitterionic surfactant is contained in the compositions according to the present invention. In the compositions according to the present invention, these ingredients possibly contribute considerably to stabilizing viscosity and storage behavior.

Particularly suitable zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Ampholytic surfactants" (Tampho) are understood as those surface-active compounds that are capable of forming internal salts. Examples of suitable ampholytic surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, having in each case approximately 8 to 24 carbon atoms in the alkyl group. Typical examples of amphoteric and zwitterionic surfactants are alkyl betaines, alkylamidobetaines, aminopropionates, aminoglycinates, imidazolinium betaines, and sulfobetaines.

Particularly preferred ampholytic surfactants are N-cocalkylaminopropionate, cocacylaminoethylaminopropionate, and $C_{12}$ to $C_{18}$ acyl sarcosine. Coco Betaine is a particularly preferred compound.

These ingredients are used in quantities from 0.01 to 5.0 wt % in terms of the total composition of the agent. Quantities from 0.05 to 5.0 wt % are preferred. Quantities from 0.1 to 5.0 wt % are particularly preferred, and from 0.3 to 3.0 wt % are highly preferred.

A third subject of the present invention is therefore a hair treatment agent containing in a suitable cosmetic carrier, based in each case on the total weight of the agent:
a) at least one cationic alkyloligoglucoside, in a total quantity from 0.01 to 10.0 wt %,
b) at least one polyglycerol ester, in a total quantity from 0.01 to 10.0 wt %, and
c) at least one quaternary ammonium compound, in a total quantity from 0.1 to 10.0 wt %, selected from at least one of the groups of
esterquats; and/or
quaternary imidazolines of formula I,

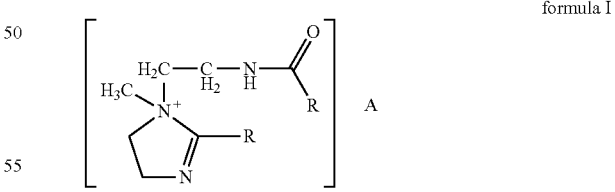

formula I in which residues R, mutually independently in each case, denote a saturated or unsaturated, linear or branched hydrocarbon residue having a chain length from 8 to 30 carbon atoms, and A denotes a physiologically acceptable anion; and/or
cetrimonium chloride and/or behentrimonium chloride; and/or
amines and/or cationized amines; and/or
poly(methacryloyloxyethyltrimethylammonium) compounds; and/or quaternized cellulose derivatives, in particular Polyquaternium-10 and/or Polyquaternium-24 and/or Polyquaternium-67 and/or Polyquaternium-72; and/or
cationized honey; and/or
cationic guar derivatives; and/or
chitosan; and/or
polymeric dimethyldiallylammonium salts and copolymers thereof with esters and amides of acrylic acid and methacrylic acid; and/or
copolymers of vinylpyrrolidone with quaternized derivatives of dialkylaminoalkyl acrylate and methacrylate; and/or
vinylpyrrolidone-vinylimidazolium methochloride copolymers; and/or
quaternized polyvinyl alcohol; and/or
Polyquaternium-2; and/or
Polyquaternium-7; and/or
Polyquaternium-16; and/or
Polyquaternium-17; and/or
Polyquaternium-18; and/or
Polyquaternium-27; and/or
Polyquaternium-69; and/or
Polyquaternium-74, and
d) at least one surfactant selected from zwitterionic and/or amphoteric surfactants, in a total quantity from 0.01 to 5.0 wt %.

All ingredients usual in cosmetic compositions can furthermore be added to this highly preferred basic framework of ingredients.

Although silicones have been used hitherto in cosmetic compositions because of their many positive properties, they are being regarded with increasing skepticism. For example, silicones often make it difficult to formulate stable emulsions, and alongside their positive properties also lead to stress on the keratinic fibers. Efforts are therefore increasingly being made to avoid this group of ingredients. Silicones can be used in the compositions according to the present invention, but they do not, surprisingly, result in any further increase in the effectiveness of the compositions according to the present invention. It is therefore possible and preferred according to the present invention to omit silicones. If silicones are nevertheless to be used, the following silicones can then be used at least with no disadvantageous influence on the compositions according to the present invention in terms of their effect.

Cationic aminosilicones having at least three terminal aminofunctional groups have only recently been offered commercially. These cationic silicone polymers are notable for the fact that they comprise a silicone skeleton as well as optionally a polyether part and furthermore at least one part having an ammonium structure. Examples of preferred cationic silicone polymers for purposes of the present invention are in particular the compounds having the INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, as well as Silicone Quaternium-2 Panthenol Succinate and Silicone Quaternium-16/Glycidyl Dimethicone Crosspolymer. Silicone Quaternium-22 is, in particular, most preferred. This raw material is marketed, for example, by the Evonik company under the commercial name Abil® T-Quat 60.

The cationic aminofunctional silicone polymers are contained in the compositions according to the present invention in quantities from 0.01 to 5 wt %, preferably in quantities from 0.05 to 5 wt %, and very particularly preferably in quantities from 0.1 to 5 wt %. The best results of all are obtained with quantities from 0.1 to 2.5 wt %, based in each case on the total composition of the respective agent.

The compositions according to the present invention can furthermore, instead of or in addition to the aminofunctional silicones just recited, contain further silicones. These silicones are preferably at least one silicone polymer selected from the group of dimethiconols and/or the group of aminofunctional silicones and/or the group of dimethicones and/or the group of cyclomethicones.

The dimethicones according to the present invention can be both linear and branched, and also cyclic or cyclic and branched. Linear dimethicones can be represented by the following structural formula (Si1):

$$(SiR^1{}_3)-O-(SiR^2{}_2-O-)_x-(SiR^1{}_3) \qquad (Si1).$$

Branched dimethicones can be represented by the structural formula (Si1.1):

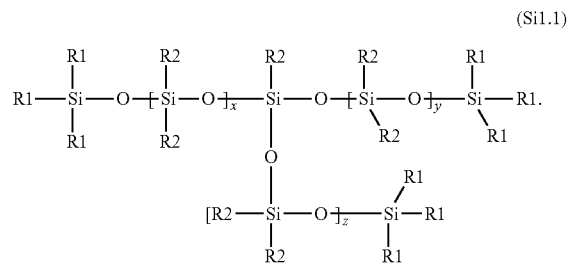

Residues R1 and R2 denote, mutually independently in each case, hydrogen, a methyl residue, a C2 to C30 linear, saturated or unsaturated hydrocarbon residue, a phenyl residue, and/or an aryl residue. The numbers x, y, and z are integers and range, mutually independently in each case, from 0 to 50,000. The molecular weights of the dimethicones are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; very particularly preferred viscosities are between 10,000 and 3,000,000 cPs. The most preferred range is between 50,000 and 2,000,000 cPs. Viscosities around the range of approximately 60,000 cPs are highly preferred. Reference may be made here, for example to the product "Dow Corning 200, 60,000 cSt."

Particularly preferred cosmetic or dermatological preparations according to the present invention are characterized in that they contain at least one silicone of formula (Si1.2)

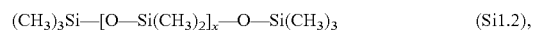

$$(CH_3)_3Si-[O-Si(CH_3)_2]_x-O-Si(CH_3)_3 \qquad (Si1.2),$$

in which x denotes a number from 0 to 100, by preference from 0 to 50, more preferably from 0 to 20, and in particular 0 to 10.

Dimethicones (Si1) are contained in the compositions according to the present invention in quantities from 0.01 to 10 wt %, by preference 0.01 to 8 wt %, particularly preferably 0.1 to 7.5 wt %, and in particular 0.1 to 5 wt %, based on the total composition.

Lastly, dimethiconols (Si8) are understood as silicone compounds. Dimethiconols according to the present invention can be both linear and branched, and also cyclic or cyclic and branched. Linear dimethiconols can be represented by the following structural formula (Si8-I):

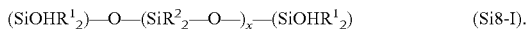

$(SiOHR^1_2)\text{—}O\text{—}(SiR^2_2\text{—}O\text{—})_x\text{—}(SiOHR^1_2)$ (Si8-I).

Branched dimethiconols can be represented by the structural formula (Si8-II):

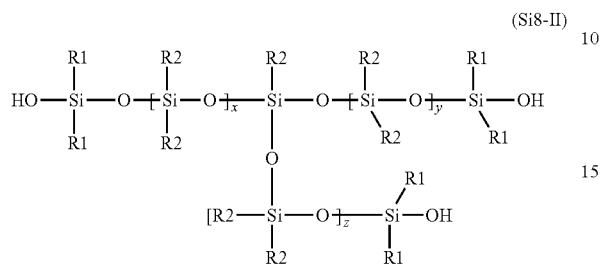

Residues $R^1$ and $R^2$ denote, mutually independently in each case, hydrogen, a methyl residue, a C2 to C30 linear, saturated or unsaturated hydrocarbon residue, a phenyl residue, and/or an aryl residue. The numbers x, y, and z are integers and range, mutually independently in each case, from 0 to 50,000. The molecular weights of the dimethicones are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; very particularly preferred viscosities are between 10,000 and 3,000,000 cPs. The most preferred range is between 50,000 and 2,000,000 cPs.

The following commercial products are recited as examples of such products: Dow Corning 1-1254 Fluid, Dow Corning 2-9023 Fluid, Dow Corning 2-9026 Fluid, Abil OSW 5 (Degussa Care Specialties), Dow Corning 1401 Fluid, Dow Corning 1403 Fluid, Dow Corning 1501 Fluid, Dow Corning 1784 HVF Emulsion, Dow Corning 9546 Silicone Elastomer Blend, SM555, SM2725, SM2765, SM2785 (all four aforesaid GE Silicones), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforesaid Wacker-Chemie GmbH).

Dimethiconols (Si8) are in the compositions according to the present invention in quantities from 0.01 to 10 wt %, by preference 0.1 to 8 wt %, particularly preferably 0.1 to 7.5 wt %, and in particular 0.1 to 5 wt % dimethiconol, based on the composition.

Particularly preferred agents according to the present invention contain one or more aminofunctional silicones. Such silicones can be described, for example, by formula (Si-2)

$M(R_aQ_bSiO_{(4-a-b)/2})_x(R_cSiO_{(4-c)/2})_yM$ (Si-2);

in the above formula,
R is a hydrocarbon or a hydrocarbon residue having 1 to approximately 6 carbon atoms,
Q is a polar residue of the general formula $R^1HZ$, in which
  $R^1$ is a divalent connecting group that is bound to hydrogen and to the Z residue, assembled from carbon and hydrogen atoms, carbon, hydrogen, and oxygen atoms, or carbon, hydrogen, and nitrogen atoms, and
Z is an organic aminofunctional residue that contains at least one aminofunctional group;

a assumes values in the range from approximately 0 to approximately 2,
b assumes values in the range from approximately 1 to approximately 3,
a+b is less than or equal to 3, and
c is a number in the range from approximately 1 to approximately 3, and
x is a number in the range from 1 to approximately 2,000, preferably from approximately 3 to approximately 50, and most preferably from approximately 3 to approximately 25, and
y is a number in the range from approximately 20 to approximately 10,000, by preference from approximately 125 to approximately 10,000, and most preferably from approximately 150 to approximately 1,000, and
M is a suitable silicone terminal group that is known in the existing art, by preference trimethylsiloxy.

Z according to formula (Si-2) is an organic aminofunctional residue containing at least one functional amino group. One possible formula for the aforesaid Z is $NH(CH_2)_zNH_2$, in which z is an integer greater than or equal to 1. Another possible formula for the aforesaid Z is $\text{—}NH(CH_2)_z(CH_2)_{zz}NH$, in which both z and zz mutually independently are an integer greater than or equal to 1, said structure encompassing diamino ring structures such as piperazinyl. The aforesaid Z is most preferably an $\text{—}NHCH_2CH_2NH_2$ residue. Another possible formula for the aforesaid Z is $\text{—}N(CH_2)_z(CH_2)_{zz}NX_2$ or $\text{—}NX_2$, in which each X is selected independently of $X_2$ from the group consisting of hydrogen and alkyl groups having 1 to 12 carbon atoms, and zz is 0.

Q according to formula (Si-2) is most preferably a polar aminofunctional residue of the formula $\text{—}CH_2CH_2CH_2NHCH_2CH_2NH_2$.

In formula (Si-2), a assumes values in the range from 0 to 2, b assumes values in the range from 2 to 3, a+b is less than or equal to 3, and c is a number in the range from 1 to 3.

Cationic silicone oils such as, for example, the commercially obtainable products Dow Corning (DC) 929 Emulsion, DC 2-2078, DC 5-7113, SM-2059 (General Electric), and SLM-55067 (Wacker) are suitable according to the present invention.

Particularly preferred agents according to the present invention are characterized in that they contain at least one aminofunctional silicone of formula (Si3-a)

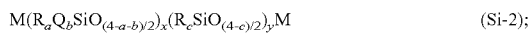

$(CH_3)_3Si\text{—}[O\text{—}Si(CH_3)_2]_n[O\text{—}Si(CH_3)_m\text{—}OSi(CH_3)_3$ (Si-3a)
$\quad\quad\quad\quad\quad\quad\quad\quad\quad\quad\quad\quad\quad\quad\quad\quad\quad |$
$\quad\quad\quad\quad\quad\quad\quad\quad\quad\quad\quad\quad\quad\quad\quad\quad CH_2CH(CH_3)CH_2NH(CH_2)_2NH_2$, in which m and n are numbers whose sum (m+n) is between 1 and 2000, by preference between 50 and 150, where n by preference assumes values from 0 to 1999 and in particular from 49 to 149, and m by preference assumes values from 1 to 2000, in particular from 1 to 10.

These silicones are referred to according to the INCI declaration as Trimethylsilylamodimethicones and are obtainable, for example, under the designation Q2-7224 (manufacturer: Dow Corning; a stabilized trimethylsilylamodimethicone).

Also particularly preferred are agents according to the present invention that contain at least one aminofunctional silicone of formula (Si-3b)

$$R\text{---}[Si(CH_3)_2\text{---}O]_{n1}[Si(R')\text{---}O]_m\text{---}[Si(CH_3)_2\text{---}O]_{n2}\text{---}SiMe_2R, \quad (Si\text{-}3b)$$
$$|$$
$$(CH_2)_3NH(CH_2)_2NH_2$$

in which

R denotes —OH, an (optionally ethoxylated and/or propoxylated) ($C_1$ to $C_{20}$) alkoxy group, or a —$CH_3$ group, $R^1$ denotes —OH, a ($C_1$ to $C_{20}$) alkoxy group, or a —$CH_3$ group, and m, n1, and n2 are numbers whose sum (m+n1+n2) is between 1 and 2000, by preference between 50 and 150, where the sum (n1+n2) by preference assumes values from 0 to 1999 and in particular from 49 to 149, and m by preference assumes values from 1 to 2000, in particular from 1 to 10.

These silicones are referred to according to the INCI declaration as Amodimethicones or as functionalized Amodimethicones, for example Bis(C13-15 Alkoxy) PG Amodimethicone (obtainable e.g. as a commercial product: DC 8500 of the Dow Corning company), Trideceth-9 PG-Amodimethicone (obtainable e.g. as a commercial product: Silcare Silicone SEA of the Clariant company).

Suitable diquaternary silicones are selected from compounds of the general formula (Si3c)

$$[R^1R^2R^3N^+\text{-}A\text{-}SiR^7R^8\text{---}(O\text{---}SiR^9R^{10})_n\text{---}O\text{---}$$
$$SiR^{11}R^{12}\text{-}A\text{-}N^+R^4R^5R^6]2X^- \quad (Si3c)$$

where residues R1 to R6 mutually independently signify C1 to C22 alkyl residues that can contain hydroxy groups, and where by preference at least one of the residues comprises at least 8 carbon atoms and the remaining residues comprise 1 to 4 carbon atoms, residues R7 to R12 mutually independently are identical or different and signify C1 to C10 alkyl or phenyl, A signifies a divalent organic connecting group, n is a number from 0 to 200, by preference from 10 to 120, particularly preferably from 10 to 40, and $X^-$ is an anion.

The divalent connecting group is by preference a C1 to C12 alkylene or alkoxyalkylene group that can be substituted with one or more hydroxyl groups.

Particularly preferably, the group is —$(CH_2)_3$—O—$CH_2$—CH(OH)—$CH_2$—.

The anion $X^-$ can be a halide ion, an acetate, an organic carboxylate, or a compound of the general formula $RSO_3^-$, in which R has the meaning of C1 to C4 alkyl residues.

A preferred diquaternary silicone has the general formula (Si3d)

$$[RN^+Me_2\text{-}A\text{-}(SiMe_2O)_n\text{---}SiMe_2\text{-}A\text{-}N^+Me_2R]$$
$$2CH_3COO^- \quad (Si3d),$$

where A is the group —$(CH_2)_3$—O—$CH_2$—CH(OH)—$CH_2$, R is an alkyl residue having at least 8 carbon atoms, and n is a number from 10 to 120.

Suitable silicone polymers having two terminal quaternary ammonium groups are known under the INCI name Quaternium-80. These are dimethylsiloxanes having two terminal trialkylammonium groups. Diquaternary polydimethylsiloxanes of this kind are marketed by the Evonik company under the commercial names Abil® Quat 3270, 3272, and 3474.

Hair treatment agents preferred according to the present invention are characterized in that they contain, based on their weight, 0.01 to 10 wt %, by preference 0.01 to 8 wt %, particularly preferably 0.1 to 7.5 wt %, and in particular 0.2 to 5 wt % aminofunctional silicone(s) and/or diquaternary silicone.

Polyammonium-polysiloxane compounds are a further silicone according to the present invention having amino functions. Polyammonium-polysiloxane compounds can be acquired, for example, from GE Bayer Silicones under the commercial name Baysilone®. The products having the designations Baysilone TP 3911, SME 253, and SFE 839 are preferred in this context. It is very particularly preferred to use Baysilone TP 3911 as an active component of the compositions according to the present invention. Polyammonium-polysiloxane compounds are used in the compositions according to the present invention in a quantity from 0.01 to 10 wt %, by preference 0.01 to 7.5, particularly preferably 0.01 to 5.0 wt %, very particularly preferably from 0.05 to 2.5 wt %, referring in each case to the total composition.

The cyclic dimethicones referred to according to INCI as Cyclomethicones are also usable with preference according to the present invention. Preferred here are cosmetic or dermatological preparations according to the present invention that contain at least one silicone of formula (Si-4)

$$\left[\begin{array}{c} Me \\ | \\ Si\text{---}O \\ | \\ Me \end{array}\right]_x \quad (Si\text{-}4)$$

in which x denotes a number from 3 to 200, by preference from 3 to 10, more preferably from 3 to 7, and in particular 3, 4, 5, or 6.

Agents likewise preferred according to the present invention are characterized in that they contain at least one silicone of formula (Si-5)

$$R_3Si\text{---}[O\text{---}SiR_2]_x\text{---}(CH_2)_n\text{---}[O\text{---}SiR_2]_y\text{---}O\text{---}SiR_3 \quad (Si\text{-}5),$$

in which R denotes identical or different residues from the group —H, phenyl, benzyl, —$CH_2$—CH($CH_3$)Ph, $C_{1\text{-}20}$ alkyl residues, by preference —$CH_3$, —$CH_2CH_3$, —$CH_2CH_2CH_3$, —CH($CH_3$)$_2$, —$CH_2CH_2CH_2H_3$, —$CH_2CH(CH_3)_2$, —CH($CH_3$)$CH_2CH_3$, —C($CH_3$)$_3$, x and/or y denotes a number from 0 to 200, by preference from 0 to 10, more preferably from 0 to 7, and in particular 0, 1, 2, 3, 4, 5, or 6, and n denotes a number from 0 to 10, preferably from 1 to 8, and in particular 2, 3, 4, 5, 6.

Besides the dimethicones, dimethiconols, amodimethicones, and/or cyclomethicones according to the present invention, water-soluble silicones can be contained in the compositions according to the present invention as further silicones.

Corresponding hydrophilic silicones are selected, for example, from compounds of formulas (Si-6) and/or (Si-7). In particular, preferred silicone-based water-soluble surfactants are selected from the group of dimethicone copolyols, which are preferably alkoxylated, in particular polyethoxylated or polypropoxylated.

"Dimethicone copolyols" are understood according to the present invention preferably as polyoxyalkylene-modified dimethylpolysiloxanes of the general formulas (Si-6) or (Si-7):

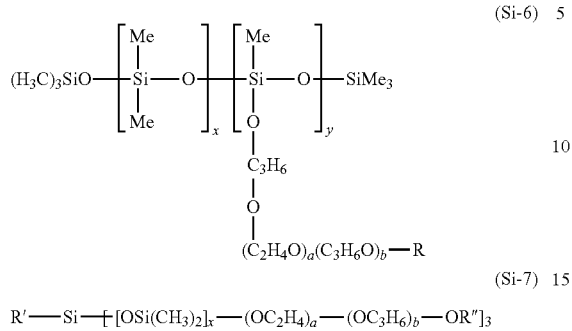

(Si-6)

(Si-7)

in which residue R denotes a hydrogen atom, an alkyl group having 1 to 12 carbon atoms, an alkoxy group having 1 to 12 carbon atoms, or a hydroxyl group, residues R' and R" signify alkyl groups having 1 to 12 carbon atoms, x denotes an integer from 1 to 100, preferably from 20 to 30, y denotes an integer from 1 to 20, preferably from 2 to 10, and a and b denote integers from 0 to 50, preferably from 10 to 30.

Particularly preferred dimethicone copolyols for purposes of the invention are, for example, the products marketed commercially under the trade name SILWET (Union Carbide Corporation) and DOW CORNING. Dimethicone copolyols particularly preferred according to the present invention are Dow Corning 190 and Dow Corning 193.

Dimethicone copolyols are in the compositions according to the present invention in quantities from 0.01 to 10 wt %, by preference 0.01 to 8 wt %, particularly preferably 0.1 to 7.5 wt %, and in particular 0.1 to 5 wt % dimethicone copolyol based on the composition.

Ester oils can be contained with particular preference as oily substances in the active substance complex according to the present invention. The ester oils are defined as follows:

"Ester oils" are to be understood as esters of $C_6$ to $C_{30}$ fatty acids with $C_2$ to $C_{30}$ fatty alcohols. The monoesters of fatty acids with alcohols having 2 to 24 carbon atoms are preferred. Examples of fatty-acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof. Examples of the fatty-alcohol components in the ester oils are isopropyl alcohol, capronyl alcohol, capryl alcohol, 2-ethylhexyl alcohol, caprinyl alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof. Isopropyl myristate (Rilanite® IPM), isononanoic acid C16-18 alkyl esters (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred according to the present invention.

The ester oils can of course also be alkoxylated with ethylene oxide, propylene oxide, or mixtures of ethylene oxide and propylene oxide. The alkoxylation can be located both on the fatty-alcohol part and on the fatty-acid part, and also on both parts, of the ester oils. It is preferred according to the present invention, however, if the fatty alcohol was first alkoxylated and then was esterified with fatty acid. Formula (D4-II) depicts these compounds in generalized fashion.

$$R1\underset{}{\overset{O}{\|}}\text{—}{+}\text{AO}{+}_{\overline{x}}\text{—}O\text{—}R2$$

(D4-II)

R1 here denotes a saturated or unsaturated, branched or unbranched, cyclic saturated or cyclic unsaturated acyl residue having 6 to 30 carbon atoms, AO denotes ethylene oxide, propylene oxide, or butylene oxide, X denotes a number between 1 and 200, by preference 1 and 100, particularly preferably between 1 and 50, very particularly preferably between 1 and 20, highly preferably between 1 and 10, and most preferably between 1 and 5, R2 denotes a saturated or unsaturated, branched or unbranched, cyclic saturated cyclic unsaturated alkyl, alkenyl, alkinyl, phenyl, or benzyl residue having 6 to 30 carbon atoms. Examples of fatty-acid components used as residue R1 in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof. Examples of the fatty-alcohol components as residue R2 in the ester oils are benzyl alcohol, isopropyl alcohol, capronyl alcohol, capryl alcohol, 2-ethylhexyl alcohol, caprinyl alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof. An ester oil that is particularly preferred according to the present invention is obtainable, for example, under the INCI name PPG-3 Benzyl Ether Myristate.

Also to be understood as ester oils are:

dicarboxylic acid esters such as di-n-butyl adipate, di-(2-ethylhexyl) adipate, di-(2-ethylhexyl) succinate, and diisotridecyl acelaate, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, neopentyl glycol dicaprylate, as well as symmetrical, asymmetrical, or cyclic esters of carbonic acid with fatty alcohols, for example glycerol carbonate or dicaprylyl carbonate (Cetiol® CC), fatty acid triesters of saturated and/or unsaturated linear and/or branched fatty acids with glycerol, fatty acid partial glycerides, i.e. monoglycerides, diglycerides, and industrial mixtures thereof. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as industrial mixtures thereof. Oleic acid monoglycerides are preferably used.

Ester oils are used in the agents according to the present invention in a quantity from 0.01 to 20 wt %, preferably 0.01 to 10.0 wt %, particularly preferably 0.01 to 7.5 wt %, highly preferably from 0.1 to 5.0 wt %. It is of course also possible according to the present invention to use several ester oils simultaneously.

Further oily substances according to the present invention are:

Vegetable oils. Examples of such oils are sunflower oil, olive oil, soybean oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as di-tert-butyl ether, diisopentyl ether, di-3-ethyldecyl ether, tert-butyl-n-octyl ether, isopentyl-n-octyl ether, and 2-methylpentyl-n-octyl ether. The compounds 1,3-di-(2-ethylhexyl)cyclohexane (Cetiol® S) and di-n-octyl ether (Cetiol® OE), available as commercial products, can be preferred.

Natural oils that are used are, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, cocoa butter, linseed oil, macadamia nut oil, corn oil, almond oil, marula oil, evening primrose oil, olive oil, palm oil, rapeseed oil, rice oil, sea buckthorn pulp oil, sea buckthorn seed oil, sesame oil, shea butter, soy oil, sunflower oil, grapeseed oil, walnut oil, wheat germ oil, or wild rose oil.

The hair treatment agents according to the present invention of course also contain, besides the active substance combination according to the present invention, further constituents usual in cosmetic compositions. Selection of these constituents is generally based on the intended use of the hair treatment agent. In the case of a shampoo, for example, further surface-active substances will be contained. In the case of hair treatments, further cationic compounds and further care-providing substances will be optionally contained. In many cases the agents contain at least one surface-active substance, both anionic as well as zwitterionic, ampholytic, nonionic, and cationic surface-active substances being suitable in principle. Selection of the surface-active substances is based on the nature of the agent.

All anionic surface-active substances suitable for use on the human body are suitable as anionic surfactants (Tanion) in preparations according to the present invention. Typical examples of anionic surfactants are:

linear and branched fatty acids having 8 to 30 carbon atoms (soaps), ether carboxylic acids of the formula R—O—(CH$_2$—CH$_2$O)$_x$—CH$_2$—COOH, in which R is a linear alkyl group having 8 to 30 carbon atoms and x=0 or is 1 to 16, and salts thereof, acyl sarcosides having 8 to 24 carbon atoms in the acyl group, acyl taurides having 8 to 24 carbon atoms in the acyl group, acyl isethionates having 8 to 24 carbon atoms in the acyl group, sulfosuccinic acid mono- and diallyl esters having 8 to 24 carbon atoms in the alkyl group, and sulfosuccinic acid monoalkylpolyoxyethyl esters having 8 to 24 carbon atoms in the alkyl group and 1 to 6 oxyethyl groups, linear alkanesulfonates having 8 to 24 carbon atoms;

linear alpha-olefinsulfonates having 8 to 24 carbon atoms, alpha-sulfo fatty acid methyl esters of fatty acids having 8 to 30 carbon atoms, alkyl sulfates and alkyl polyglycol ether sulfates of the formula R—O(CH$_2$—CH$_2$—O)$_x$—OSO$_3$H, in which R is a preferably linear alkyl group having 8 to 30 carbon atoms and x=0 or is 1 to 12, hydroxysulfonates substantially corresponding to at least one of the two following formulas, or mixtures thereof, as well as salts thereof:

CH$_3$—(CH$_2$)$_y$—CHOH—(CH$_2$)$_p$—(CH—SO$_3$M)-(CH$_2$)$_z$—CH$_2$—O—(C$_n$H$_{2n}$O)$_x$—H, and/or CH$_3$—(CH$_2$)$_y$—(CH—SO$_3$M)-(CH$_2$)$_p$—CHOH—(CH$_2$)$_z$—CH$_2$—O—(C$_n$H$_{2n}$O)$_x$—H, such that in both formulas y and z=0 or are integers from 1 to 18, p=0, 1, or 2, and the sum (y+z+p) is a number from 12 to 18, x=0 or is a number from 1 to 30, and n is an integer from 2 to 4, and M=H or an alkali metal ion, in particular sodium, potassium, lithium, an alkaline earth metal ion, in particular magnesium, calcium, zinc, and/or an ammonium ion, which optionally can be substituted, in particular mono-, di-, tri- or tetraammonium ions having C1 to C4 alkyl, alkenyl, or aryl residues, sulfated hydroxyalkylpolyethylene glycol ethers and/or hydroxyalkylenepropylene glycol ethers of the formula R$^1$—(CHOSO$_3$M)-CHR$^3$—(OCHR$^4$—CH$_2$)n-OR$^2$, where R$^1$ denotes a linear alkyl residue having 1 to 24 carbon atoms, R$^2$ a linear or branched, saturated alkyl residue having 1 to 24 carbon atoms, R$^3$ denotes hydrogen or a linear alkyl residue having 1 to 24 carbon atoms, R$^4$ denotes hydrogen or a methyl residue, and M denotes hydrogen ion, ammonium ion, alkylammonium ion, or alkanolammonium ion, in which the alkyl and alkanol residues each comprise 1 to 4 carbon atoms, or a cationic metal atom selected from lithium ion, sodium ion, potassium ion, calcium ion, Of and magnesium ion, and n denotes a number in the range from 0 to 12, and furthermore the total number of carbon atoms contained in R$^1$ and R$^3$ is 2 to 44, sulfonates of unsaturated fatty acids having 8 to 24 carbon atoms and 1 to 6 double bonds, esters of tartaric acid and citric acid with alcohols that represent addition products of approximately 2 to 15 molecules of ethylene oxide and/or propylene oxide with fatty alcohols having 8 to 22 carbon atoms, alkyl and/or alkenyl ether phosphates of the formula

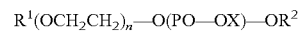

in which R$^1$ preferably denotes an aliphatic hydrocarbon residue having 8 to 30 carbon atoms, R$^2$ denotes hydrogen, a (CH$_2$CH$_2$O)$_n$R$^2$ residue, or X, n denotes numbers from 1 to 10, and X denotes a hydrogen ion, an alkali or alkaline-earth metal ion, or NR$^3$N$^4$N$^5$N$^6$, where R$^3$ to R$^6$ mutually independently denote hydrogen or a C$_1$ to C$_4$ hydrocarbon residue, sulfated fatty acid alkylene glycol esters of the formula RCO(AlkO)$_n$SO$_3$M, in which RCO— denotes a linear or branched, aliphatic, saturated and/or unsaturated acyl residue having 6 to 22 carbon atoms, Alk denotes $CH_2CH_2$, $CHCH_3CH_2$, and/or $CH_2CHCH_3$, n denotes numbers from 0.5 to 5, and M denotes a cation selected from an alkali metal ion, in particular sodium ion, potassium ion, or lithium ion, an alkaline-earth metal, in particular magnesium or calcium, a zinc ion, and an ammonium ion such as $^+NR^3N^4N^5N^6$, where $R^3$ to $R^6$ mutually independently denote hydrogen or a $C_1$ to $C_4$ hydrocarbon residue, monoglyceride sulfates and monoglyceride ether sulfates of the formula $R^8OC-(OCH_2CH_2)_x-OCH_2-[CHO(CH_2CH_2O)_yH]-CH_2O(CH_2CH_2O)_z-SO_3X$, in which $R^8CO$ denotes a linear or branched acyl residue having 6 to 22 carbon atoms, x, y, and z in total denote 0 or numbers from 1 to 30, preferably 2 to 10, and X denotes an alkali or alkaline-earth metal. Typical examples of monoglyceride (ether) sulfates suitable for purposes of the invention are the reaction products of lauric acid monoglyceride, coconut fatty acid monoglyceride, palmitic acid monoglyceride, stearic acid monoglyceride, oleic acid monoglyceride, and tallow fatty acid monoglyceride, and their ethylene oxide adducts with sulfur trioxide or chlorosulfonic acid in the form of their sodium salts. It is preferable to use monoglyceride sulfates in which $R^8CO$ denotes a linear acyl residue having 8 to 18 carbon atoms, amide ether carboxylic acids, $R^1-CO-NR^2-CH_2CH_2-O-(CH_2CH_2O)_nCH_2COOM$ where $R^1$ is a straight-chain or branched alkyl or alkenyl residue having a number of carbon atoms in the chain from 2 to 30, n denotes an integer from 1 to 20, and $R^2$ denotes hydrogen, a methyl, ethyl, propyl, isopropyl, n-butyl, tert-butyl, or isobutyl residue and M denotes a hydrogen ion or a metal, such as an alkali metal, in particular sodium, potassium, lithium, an alkaline-earth metal, in particular magnesium, calcium, zinc, or an ammonium ion such as $^+NR^3N^4N^5N^6$, where $R^3$ to $R^6$ mutually independently denote hydrogen or a $C_1$ to $C_4$ hydrocarbon residue. Products of this kind are obtainable, for example, from the Chem-Y company under the product designation Akypo®.

Acyl glutamates of the formula $XOOC-CH_2CH_2CH(C(NH)OR)-COOX$, in which RCO denotes a linear or branched acyl residue having 6 to 22 carbon atoms and 0 and/or 1, 2, or 3 double bonds, and X denotes hydrogen, an alkali and/or alkaline-earth metal, ammonium, alkylammonium, alkanolammonium, or glucammonium, condensation products of a water-soluble salt of a water-soluble protein hydrolysate with a C8 to C30 fatty acid. Such products have been obtainable for some time under the trade names Lamepon®, Maypon®, Gluadin®, Hostapon® KCG, or Amisoft®, alkyl- and/or alkenyloligoglycoside carboxylates, sulfates, phosphates, and/or isethionates, acyl lactates, and hydroxy mixed ether sulfates.

If the mild anionic surfactants contain polyglycol ether chains, it is very particularly preferred that they exhibit a restricted homolog distribution. It is further preferred in the case of mild anionic surfactants having polyglycol ether units that the number of glycol ether groups be equal to 1 to 20, preferably 2 to 15, particularly preferably 2 to 12. Particularly mild anionic surfactants having polyglycol ether groups without a restricted homolog distribution can also be obtained, for example, if on the one hand the number of polyglycol ether groups is equal to 4 to 12, and Zn or Mg ions are selected as a counter ion. One example thereof is the commercial product Texapon® ASV.

Nonionic surfactants (Tnio) are, for example, addition products of 2 to 50 mol ethylene oxide and/or 0 to 5 mol propylene oxide with linear and branched fatty alcohols having 6 to 30 carbon atoms, fatty alcohol polyglycol ethers, fatty alcohol polypropylene glycol ethers, and mixed fatty alcohol polyethers, addition products of 2 to 50 mol ethylene oxide and/or 0 to 5 mol propylene oxide with linear and branched fatty acids having 6 to 30 carbon atoms, fatty acid polyglycol ethers, fatty acid polypropylene glycol ethers, and mixed fatty acid polyethers, addition products of 2 to 50 mol ethylene oxide and/or 0 to 5 mol propylene oxide with linear and branched alkylphenols having 8 to 15 carbon atoms in the alkyl group, alkylphenol polyglycol ethers, alkylphenol polypropylene glycol ethers, and mixed alkylphenol polyethers, addition products, end-capped with a methyl or $C_2$ to $C_6$ alkyl group, of 2 to 50 mol ethylene oxide and/or 0 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as, for example, the grades obtainable under the marketing designations Dehydrol® LS, Dehydrol® LT (Cognis), $C_{12}$ to $C_{30}$ fatty acid mono- and diesters of addition products of 1 to 30 mol ethylene oxide with glycerol, addition products of 5 to 60 mol ethylene oxide with castor oil and hardened castor oil, polyol fatty acid esters such as, for example, the commercial product Hydagen®HSP (Cognis), or Sovermol® grades (Cognis), alkoxylated triglycerides, alkoxylated fatty acid alkyl esters of formula (Tnio-I):

$$R^1CO-(OCH_2CHR^2)_wOR^3 \quad \text{(Tnio-I)},$$

in which $R^1CO$ denotes a linear or branched, saturated and/or unsaturated acyl residue having 6 to 22 carbon atoms, $R^2$ denotes hydrogen or methyl, $R^3$ denotes linear or branched alkyl residues having 1 to 4 carbon atoms, and w denotes numbers from 1 to 20, amine oxides, hydroxy mixed ethers, $R^1O[CH_2CH(CH_3)O]_x(CH_2CHR^2O)_y[CH_2CH(OH)R^3]_z$ where $R^1$ denotes a linear or branched, saturated or unsaturated alkyl and/or alkenyl residue having 2 to 30 carbon atoms, $R^2$ denotes hydrogen, a methyl, ethyl, propyl, or isopropyl residue, $R^3$ denotes a linear or branched alkyl residue having 2 to 30 carbon atoms, x denotes 0 or a number from 1 to 20, Y denotes a number from 1 to 30, and z denotes the number 1, 2, 3, 4 or 5, sorbitan fatty acid esters and addition products of ethylene oxide with sorbitan fatty acid esters, for example the polysorbates, sugar fatty acid esters and addition products of ethylene oxide with sugar fatty acid esters, addition products of ethylene oxide with fatty acid alkanolamides and fatty amines, sugar surfactants of the alkyl- and alkenyloligoglycoside types, sugar surfactants of the fatty acid N-alkylpolyhydroxyalkylamide types, fatty acid amide polyglycol ethers, fatty amine polygycol ethers, mixed ethers, mixed formals and polysorbates.

Surfactants (T) are used in quantities from 0.05 to 45 wt %, preferably 0.1 to 30 wt %, and very particularly preferably from 0.5 to 25 wt %, based on the total agent used according to the present invention.

Emulsifier agents usable according to the present invention are, for example:
- addition products of 4 to 30 mol ethylene oxide and/or 0 to 5 mol propylene oxide with linear fatty alcohols having 8 to 22 carbon atoms, with fatty acids having 12 to 22 carbon atoms, and with alkylphenols having 8 to 15 carbon atoms in the alkyl group,
- $C_{12}$ to $C_{22}$ fatty acid mono- and diesters of addition products of 1 to 30 mol ethylene oxide with polyols having 3 to 6 carbon atoms, in particular with glycerol,
- addition products of ethylene oxide and polyglycerol with methyl glucoside fatty acid esters, fatty acid alkanolamides, and fatty acid glucamides,
- $C_8$ to $C_{22}$ alkyl mono- and oligoglycosides and ethoxylated analogs thereof, where degrees of oligomerization from 1.1 to 5, in particular 1.2 to 2.0, and glucose as a sugar component, are preferred,
- mixtures of alkyl (oligo)glucosides and fatty alcohols, for example the commercially obtainable product Montanov® 68,
- addition products of 5 to 60 mol ethylene oxide with castor oil and hardened castor oil,
- partial esters of polyols having 3 to 6 carbon atoms with saturated fatty acids having 8 to 22 carbon atoms,
- sterols, both from animal tissue (zoosterols, cholesterol, lanosterol) and from vegetable fats (phytosterols, ergosterol, stigmasterol, sitosterol), or from fungi and yeasts (mycosterols),
- phospholipids (lecithins, phosphatidylcholines),
- fatty acid esters of sugars and sugar alcohols, such as sorbitol,
- polyglycerols and polyglycerol derivatives such as e.g. polyglycerol-12-hydroxystearate (commercial product Dehymuls® PGPH).

The agents according to the present invention contain emulsifier agents preferably in quantities from 0.1 to 25 wt %, in particular 0.5 to 15 wt %, based on the total agent.

With particular preference, the compositions according to the present invention contain fatty substances (Fat) as a further active substance. "Fatty substances" (Fat) are to be understood as fatty acids, fatty alcohols, natural and synthetic waxes, which can be present both in solid form and in liquid form in aqueous dispersion, and natural and synthetic cosmetic oil components.

The fatty acids (Fatac) that can be used are linear and/or branched, saturated and/or unsaturated fatty acids having 6 to 30 carbon atoms. Fatty acids having 10 to 22 carbon atoms are preferred. Among those that might be recited are, for example, isostearic acids, such as the commercial products Emersol® 871 and Emersol® 875, and isopalmitic acids such as the commercial product Edenor® IP 95, as well as all other fatty acids marketed under the Edenor® commercial designations (Cognis). Further typical examples of such fatty acids are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof. The fatty acid cuts that are obtainable from coconut oil or palm oil are usually particularly preferred; the use of stearic acid is, as a rule, particularly preferred.

The quantity used is 0.1 to 15 wt % based on the total agent. The quantity is preferably 0.5 to 10 wt %, and quantities from 1 to 5 wt % can be very particularly advantageous.

Fatty alcohols (Fatal) that can be used are saturated, mono- or polyunsaturated, branched or unbranched fatty alcohols having $C_6$ to $C_{30}$, preferably $C_{10}$ to $C_{22}$, and very particularly preferably $C_{12}$ to $C_{22}$ carbon atoms. Usable in the context of the invention are, for example, decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, caprinyl alcohol, linoleyl alcohol, linolenyl alcohol, and behenyl alcohol, as well as Guerbet alcohols thereof, this listing being intended to be exemplary and not limiting in nature. Fatty alcohols derive, however, from preferably natural fatty acids; it is usually possible to proceed by recovery from the esters of the fatty acids by reduction. Also usable according to the present invention are those fatty acid cuts that represent a mixture of different fatty alcohols. Such substances are, for example, available for purchase under the designations Stenol®, e.g. Stenol® 1618, or Lanette®, e.g. Lanette® O, or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16, or Isocarb® 24. It is of course also possible according to the present invention to use wool-wax alcohols such as those available for purchase under the designations Corona®, White Swan®, Coronet®, or Fluilan®. The fatty alcohols are used in quantities from 0.1 to 30 wt % based on the total preparation, preferably in quantities from 0.1 to 20 wt %.

Natural or synthetic waxes (Fatwax) that can be used according to the present invention are solid paraffins or iso-paraffins, carnauba waxes, beeswaxes, candelilla waxes, ozocerites, ceresin, spermaceti, sunflower wax, fruit waxes such as, for example, apple wax or citrus wax, microcrystalline waxes made from PE or PP. Such waxes are obtainable, for example, via Kahl & Co., Trittau.

The quantity used is 0.1 to 50 wt % based on the total agent, preferably 0.1 to 20 wt %, and particularly preferably 0.1 to 15 wt % based on the total agent.

The total quantity of oil and fat components in the agents according to the present invention is usually 0.5 to 75 wt %, based on the total agent. Quantities from 0.5 to 35 wt % are preferred according to the present invention.

Protein hydrolysates and/or derivatives thereof are a further synergistic active substance according to the present invention in the compositions according to the present invention having the active substance complex according to the present invention.

According to the present invention, protein hydrolysates of both vegetable and animal origin, or of marine or synthetic origin, can be used.

Animal protein hydrolysates are, for example, protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), and Kerasol® (Croda).

Also preferred according to the present invention are vegetable protein hydrolysates such as, for example, soy, almond, pea, moringa, potato, and wheat protein hydrolysates. Such products are obtainable, for example, under the trademarks Gluadin®(Cognis), DiaMin® (Diamalt), Lexein® (Inolex), Hydrosoy® (Croda), Hydrolupin®(Croda), Hydrosesame® (Croda), Hydrotritium® (Croda), Crotein® (Croda), and Puricare® LS 9658 of the Laboratoires Sdrobiologiques company.

Further protein hydrolysates preferred according to the present invention are of marine origin. These include, for example, collagen hydrolysates from fish or algae, as well as protein hydrolysates from mussels and pearl hydrolysates. Examples of pearl extracts according to the present invention are the commercial products Pearl Protein Extract BG® or Crodarom® Pearl.

Cationized protein hydrolysates are further to be included among the protein hydrolysates and derivatives thereof, in which context the underlying protein hydrolysate can derive from animals, for example from collagen, milk, or keratin, from plants, for example from wheat, corn, rice, potatoes, soy, or almonds, from marine life forms, for example from fish collagen or algae, or from biotechnologically obtained protein hydrolysates. Typical examples that may be recited of cationic protein hydrolysates and derivatives according to the present invention are the products listed under the INCI names in the "International Cosmetic Ingredient Dictionary and Handbook" (seventh edition 1997, The Cosmetic, Toiletry, and Fragrance Association, 1101 17th Street, N.W., Suite 300, Washington, D.C. 20036-4702), and available commercially.

The protein hydrolysates are contained in the compositions in concentrations from 0.001 wt % to 20 wt %, by preference from 0.05 wt % to 15 wt %, and very particularly preferably in quantities from 0.05 wt % to 5 wt %.

A further preferred group of ingredients of the compositions according to the present invention having the active substance complex according to the present invention is vitamins, provitamins, or vitamin precursors. Vitamins, provitamins, and vitamin precursors that are allocated to groups A, B, C, E, F, and H are particularly preferred.

The group of substances referred to as "vitamin A" includes retinol (vitamin $A_1$) as well as 3,4-didehydroretinol (vitamin $A_2$). β-Carotene is the provitamin of retinol. Vitamin A components that are suitable according to the present invention are, for example, vitamin A acid and esters thereof, vitamin A aldehyde, and vitamin A alcohol, as well as esters thereof such as the palmitate and acetate. The agents according to the present invention contain the vitamin A component preferably in quantities from 0.05 to 1 wt %, based on the total preparation.

Members of the vitamin B group or vitamin B complex are, among others:

Vitamin $B_1$ (thiamine)
Vitamin $B_2$ (riboflavin)
Vitamin $B_3$. The compounds nicotinic acid and nicotinic acid amide (niacinamide) are often listed under this designation. Nicotinic acid amide is preferred according to the present invention; it is contained in the agents used according to the present invention preferably in quantities from 0.05 to 1 wt % based on the total agent.
Vitamin $B_5$ (pantothenic acid, panthenol, and pantolactone). In the context of this group, panthenol and/or pantolactone are preferably used. Derivatives of panthenol that are usable according to the present invention are, in particular, the esters and ethers of panthenol as well as cationically derivatized panthenols. Individual representatives are, for example, panthenol triacetate, panthenol monoethyl ether and the monoacetate thereof, as well as cationic panthenol derivatives.

Pantothenic acid is used in the present invention preferably as a derivative in the form of more-stable calcium salts and sodium salts (calcium pantothenate, sodium pantothenate).
Vitamin $B_6$ (pyridoxine as well as pyridoxamine and pyridoxal).

The aforesaid compounds of the vitamin B type, in particular vitamin $B_3$, $B_5$, and $B_6$, are contained in the agents according to the present invention preferably in quantities from 0.05 to 10 wt % based on the total agent. Quantities from 0.1 to 5 wt % are particularly preferred.

Vitamin C (ascorbic acid). Vitamin C is utilized in the agents according to the present invention preferably in quantities from 0.1 to 3 wt % based on the total agent. Utilization in the form of the palmitic acid ester, the glucosides, or the phosphates can be preferred. Utilization in combination with tocopherols can likewise be preferred.

Vitamin E (tocopherols, in particular α-tocopherol). Tocopherol and its derivatives, which include in particular esters such as the acetate, nicotinate, phosphate, and succinate, are contained in the agents according to the present invention preferably in quantities from 0.05 to 1 wt % based on the total agent.

Vitamin F. The term "vitamin F" is usually understood to mean essential fatty acids, in particular linoleic acid, linolenic acid, and arachidonic acid.

Vitamin H. "Vitamin H" refers to the compound (3aS,4S, 6aR)-2-oxohexahydrothienol[3,4-d]-imidazole-4-valeric acid, for which the trivial name "biotin" has, however, now become established. Biotin is contained in the agents according to the present invention preferably in quantities from 0.0001 to 1.0 wt %, in particular in quantities from 0.001 to 0.01 wt %.

The compositions according to the present invention preferably contain vitamins, provitamins, and vitamin precursors from groups A, B, E, and H. Panthenol, pantolactone, pyridoxine and its derivatives, as well as nicotinic acid amide and biotin, are particularly preferred.

A particularly preferred group of ingredients in the cosmetic compositions according to the present invention is the betaines recited as follows: carnitine, carnitine nitrate, carnitine magnesium citrate, acetylcarnitine, betalaine, 1,1-dimethylproline, choline, choline chloride, choline bitartrate, choline hydrogen citrate, and the compound N,N,N-trimethylglycine referred to in the literature as "betaine."

In a further embodiment preferred according to the present invention, the compositions according to the present invention contain bioquinones. In agents according to the present invention, "suitable bioquinones" are to be understood as one or more ubiquinone(s) and/or plastoquinone(s). The ubiquinones preferred according to the present invention have the following formula:

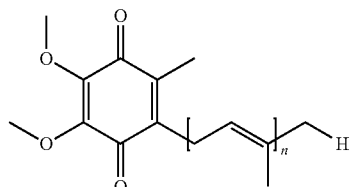

where $n$ = 6, 7, 8, 9, or 10.

Coenzyme Q-10 is most preferred in this context.
Preferred compositions according to the present invention contain purine and/or purine derivatives within narrower quantitative ranges. Cosmetic agents preferred according to the present invention are characterized here in that they contain, based on their weight, 0.001 to 2.5 wt %, by preference 0.0025 to 1 wt %, particularly preferably 0.005 to 0.5 wt %, and in particular 0.01 to 0.1 wt % purine(s) and/or purine derivative(s). Cosmetic agents preferred according to the present invention are characterized in that they contain purine, adenine, guanine, uric acid, hypoxanthine, 6-purinethiol, 6-thioguanine, xanthine, caffeine, theobromine, or theophylline. In hair-cosmetic preparations, caffeine is most preferred.

In a further preferred embodiment of the present invention, the cosmetic agent contains ectoin ((S)-2-methyl-1,4,5,6-tetrahydro-4-pyrimidinecarboxylic acid).

Agents that contain, based on their weight, 0.00001 to 10.0 wt %, by preference 0.0001 to 5.0 wt %, and in particular 0.001 to 3 wt % active substances from the group constituted by carnitine, coenzyme Q-10, ectoin, a vitamin of the B series, a purine, and derivatives or physiologically acceptable salts thereof, are particularly preferred according to the present invention.

A very particularly preferred care-providing additive in the hair treatment agents according to the present invention is taurine. "Taurine" is understood exclusively as 2-aminoethanesulfonic acid, and a "derivative" as the explicitly recited derivatives of taurine. "Derivatives of taurine" are understood as N-monomethyltaurine, N,N-dimethyltaurine, taurine lysylate, taurine tartrate, taurine ornithate, lysyl taurine, and ornithyl taurine.

Agents according to the present invention that contain, based on their weight, 0.0001 to 10.0 wt %, by preference 0.0005 to 5.0 wt %, particularly preferably 0.001 to 2.0 wt %, and in particular 0.001 to 1.0 wt % taurine and/or a derivative of taurine are particularly preferred.

The effect of the compositions according to the present invention can be further enhanced by means of a 2-pyrrolidinone-5-carboxylic acid and derivatives thereof. The sodium, potassium, calcium, magnesium, or ammonium salts, in which the ammonium ion carries, beside hydrogen, one to three $C_1$ to $C_4$ alkyl groups, are preferred. The sodium salt is very particularly preferred. The quantities used in the agents according to the present invention are 0.05 to 10 wt %, based on the total agent, particularly preferably 0.1 to 5, and in particular 0.1 to 3 wt %.

The use of plant extracts as care-providing substances allows the hair treatment agents according to the present invention to be formulated in particularly near-natural fashion but nevertheless very effectively in terms of their care-providing performance. It can in fact be possible to dispense with preservatives that are otherwise usual. Preferred above all according to the present invention are the extracts from green tea, oak bark, stinging nettle, witch hazel, hops, henna, chamomile, burdock, horsetail, whitethorn, linden blossom, almond, aloe vera, pine, horse chestnut, sandalwood, juniper, coconut, mango, apricot, lemon, wheat, kiwi, melon, orange, grapefruit, sage, rosemary, birch, mallow, valerian, lady's smock, wild thyme, yarrow, thyme, melissa, restharrow, coltsfoot, hibiscus, meristem, ginseng, coffee, cocoa, moringa, ginger root and Ayurvedic plant extracts such as for example *Aegle marmelos* (bilwa), *Cyperus rotundus* (nagar motha), *Emblica officinalis* (amalki), *Morida citrifolia* (ashyuka), *Tinospora cordifolia* (guduchi), *Santalum album* (chandana), *Crocus sativus* (kumkuma), *Cinnamonum zeylanicum*, and *Nelumbo nucifera* (kamala), sweet grasses such as wheat, barley, rye, oats, spelt, corn, the various types of millet (proso millet, finger millet, foxtail millet as examples), sugar cane, ryegrass, meadow foxtail, false oat-grass, bentgrass, meadow fescue, moor grass, bamboo, cottongrass, pennisetums, Andropogonodeae (*Imperata cylindrica*, also known as blood grass or cogon grass), buffalo grass, cord grass, dog's tooth grass, lovegrass, *Cymbopogon* (citronella grass), *Oryzeae* (rice), *Zizania* (wild rice), marram grass, blue oatgrass, softgrasses, quaking grasses, speargrasses, couch grasses and *Echinacea*, in particular *Echinacea purpurea* (L.) Moench, all types of vine, and pericarp of *Litchi chinensis*.

The plant extracts can be used according to the present invention in both pure and dilute form. If they are used in dilute form, they usually contain approx. 2 to 80 wt % active substance and, as a solvent, the extraction agent or extraction agent mixture used to recover them.

It can occasionally be necessary to use anionic polymers. Examples of anionic monomers from which such polymers can be made are acrylic acid, methacrylic acid, crotonic acid, maleic acid anhydride, and 2-acrylamido-2-methylpropanesulfonic acid. The acid groups in this context can be present entirely or partly as a sodium, potassium, ammonium, mono- or triethanolammonium salt. Preferred monomers are 2-acrylamido-2-methylpropanesulfonic acid and acrylic acid.

Anionic polymers that contain 2-acrylamido-2-methylpropanesulfonic acid as the only monomer or co-monomer have proven to be very particularly effective, in which context the sulfonic acid group can be present entirely or partly as a sodium, potassium, ammonium, mono- or triethanolammonium salt.

The homopolymer of 2-acrylamido-2-methylpropanesulfonic acid that is obtainable commercially, for example, under the designation Rheothik® 11-80 is particularly preferred.

Preferred nonionogenic monomers are acrylamide, methacrylamide, acrylic acid ester, methacrylic acid ester, vinylpyrrolidone, vinyl ether, and vinyl ester.

Preferred anionic copolymers are acrylic acid/acrylamide copolymers as well as, in particular, polyacrylamide copolymers with sulfonic-acid-group-containing monomers. A polymer of this kind is contained in the commercial product Sepigel® 305 of the SEPPIC company.

Anionic homopolymers that are likewise preferred are uncrosslinked and crosslinked polyacrylic acids. Allyl ethers of pentaerythritol, of sucrose, and of propylene can be preferred crosslinking agents. Such compounds are obtainable commercially, for example, under the trademark Carbopol®.

Copolymers of maleic acid anhydride and methylvinyl ether, in particular those having crosslinks, are also color-preserving polymers. A maleic acid/methylvinyl ether copolymer crosslinked with 1,9-decadiene is obtainable commercially under the designation Stabileze® QM.

Anionic polymers are contained in the agents according to the present invention preferably in quantities from 0.05 to 10 wt %, based on the total agent. Quantities from 0.1 to 5 wt % are particularly preferred.

In a further embodiment, the agents according to the present invention can contain nonionogenic polymers.

Suitable nonionogenic polymers are, for example:

Vinylpyrrolidone/vinyl ester copolymers such as those marketed, for example, under the trademark Luviskol® (BASF). Luviskol® VA 64 and Luviskol® VA 73, which are each vinylpyrrolidone/vinyl acetate copolymers, are likewise preferred nonionic polymers.

Cellulose ethers such as hydroxypropyl cellulose, hydroxyethyl cellulose, and methylhydroxypropyl cellulose, such as those marketed, for example, under the trademarks Culminal® and Benecel® (AQUALON) and Natrosol® grades (Hercules).

Starch and derivatives thereof, in particular starch ethers, for example Structure® XL (National Starch), a multifunctional, salt-tolerant starch, shellac, polyvinylpyrrolidones such as those marketed, for example, under the designation Luviskol® (BASF).

Nonionic polymers are contained in the compositions according to the present invention preferably in quantities from 0.05 to 10 wt %, based on the total agent. Quantities from 0.1 to 5 wt % are particularly preferred.

In a further embodiment, the agents according to the present invention should additionally contain at least one UV light protection filter. UVB filters can be oil-soluble or water-soluble.

The following are to be recited, for example, as oil-soluble substances:

3-benzylidene camphor, e.g. 3-(4-methylbenzylidene) camphor, 4-aminobenzoic acid derivatives, by preference 4-(dimethylamino)benzoic acid 2-ethylhexyl ester, 4-(dimethylamino)benzoic acid amyl ester, and 4-(dimethylamino)benzoic acid ester, esters of cinnamic acid, by preference 4-methoxycinnamic acid 2-ethylhexyl ester, 4-methoxycinnamic acid propyl ester, 4-methoxycinnamic acid isoamyl ester, 2-cyano-3-phenylcinnamic acid 2-ethylhexyl ester (octocrylene), esters of salicylic acid, by preference salicylic acid 2-ethylhexyl ester, salicylic acid 4-isopropylbenzyl ester, salicylic acid homomethyl ester, derivatives of benzophenone, by preference 2-hydroxy-4-methoxybenzophenone, 2-hydroxy-4-methoxy-4'-methylbenzophenone, 2,2'-dihydroxy-4-methoxybenzophenone, esters of benzalmalonic acid, by preference 4-methoxybenzalmalonic acid di-2-ethylhexyl ester, triazine derivatives such as e.g. 2,4,6-trianilino-(p-carbo-2'-ethyl-1'-hexyloxy)-1,3,5-triazine and octyltriazone, propane-1,3-diones, such as e.g. 1-(4-tert-butylphenyl)-3-(4'-methoxyphenyl)propane-1,3-dione.

Suitable water-soluble substances are:

2-phenylbenzimidazole-5-sulfonic acid and alkali, alkaline-earth, ammonium, alkylammonium, alkanolammonium, and glucammonium salts thereof, sulfonic acid derivatives of benzophenones, by preference 2-hydroxy-4-methoxybenzophenone-5-sulfonic acid and salts thereof, sulfonic acid derivatives of 3-benzylidene camphor such as, for example, 4-(2-oxo-3-bornylidenemethyl)benzenesulfonic acid and 2-methyl-5-(2-oxo-3-bornylidene) sulfonic acid and salts thereof.

Typical UV-A filters that are suitable are, in particular, derivatives of benzoylmethane, for example 1-(4'-tert-butylphenyl)-3-(4'-methoxyphenyl)propane-1,3-dione or 1-phenyl-3-(4'-isopropylphenyl)propane-1,3-dione. The UV-A and UV-B filters can, of course, also be used in mixtures. In addition to the soluble substances recited, insoluble pigments are also suitable for this purpose, in particular finely dispersed metal oxides and/or salts such as e.g. titanium oxide, zinc oxide, iron oxide, aluminum oxide, cerium oxide, zirconium oxide, silicates (talc), barium sulfate, and zinc stearate. The particles should have an average diameter of less than 100 nm, by preference between 5 and 50 nm, and in particular between 15 and 30 nm. They can have a spherical shape, but those particles that possess an ellipsoidal shape or one otherwise deviating from a spherical form can also be used.

The cosmetic agents can additionally contain further active substances, adjuvants, and additives such as, for example:

structuring agents such as maleic acid and lactic acid, swelling agents such as urea, allantoin, carbonates, or hydantoin, dimethylisosorbide and cyclodextrins, dyes for coloring the agent, anti-dandruff active substances such as piroctone olamide, zinc omadine, and climbazole, complexing agents such as EDTA, NTA, β-alaninediacetic acid, and phosphonic acids, opacifiers such as latex, styrene/PVP and styrene/acrylamide copolymers, luster agents such as ethylene glycol mono- and distearate as well as PEG-3 distearate, pigments, stabilizing agents for hydrogen peroxide and other oxidizing agents, propellants such as propane/butane mixtures, $N_2O$, dimethyl ether, $CO_2$, and air, antioxidants perfume oils, scents, and fragrances.

With regard to further optional components as well as the quantities of those components used, reference is made expressly to the relevant manuals known to one skilled in the art.

A further subject of the invention is therefore a method for hair treatment in which a hair treatment agent according to Claim 1 is applied onto the hair and is rinsed out of the hair after a contact time.

The contact time is preferably from a few seconds to 100 minutes, particularly preferably 1 to 50 minutes, and very particularly preferably 1 to 30 minutes.

Also in accordance with the invention is a method in which a cosmetic agent according to Claim 1 is applied onto the hair and remains there. "Remains on the hair" is understood according to the present invention to mean that the agent is not rinsed out of the hair again immediately after it is applied. Instead, in this case the agent remains on the hair for more than 100 minutes, until the hair is next washed.

Lastly, use of a composition as described above to reduce and/or delay dandruff on the scalp is in accordance with the invention. Finally, use of a composition as described above to enhance skin compatibility, in particular compatibility of the compositions on the scalp, is in accordance with the invention.

The Examples below are intended to explain the subject matter of the present invention without, however, limiting it.

Examples

All quantitative indications are parts by weight unless otherwise noted. The following formulations were made available using known manufacturing methods.

Demonstration of Effect

The compositions listed below were prepared using usual manufacturing methods. As a test method, on the one hand a turbidity measurement was performed at room temperature (23° C.) using a spectrophotometer (Lico 400) to measure the transmittance of the preparations. The compositions were also sprayed onto the dry hair of 10 test subjects, the comparison formulation on one half and the formulation according to the present invention on the other half in each case. Immediately after spraying and after one hour, the subjects were asked for their perceptions with regard to the occurrence of itching on the scalp.

|  | V1 | E1 | E1 |
| --- | --- | --- | --- |
| Lactic acid (80%) | 0.47 | 0.47 | 0.47 |
| Polyquaternium-10 | 0.4 | 0.4 | 0.4 |
| Cetrimonium chloride | 1.0 | 1.0 | 1.0 |
| Sodium benzoate | 0.1 | 0.1 | 0.1 |
| Polyquaternium-77 | 0.5 | 0.5 | 0.5 |
| Glycerol | 2.0 | 2.0 | 2.0 |
| Marine Hydrolyzed Collagen | 0.2 | 0.2 | 0.2 |
| D-panthenol (75%) | 0.2 | 0.2 | 0.2 |
| Keratin hydrolysate | 0.02 | 0.02 | 0.02 |
| PVP/VA Copolymer | 1.0 | 1.0 | 1.0 |
| Hydrogenated Castor Oil, 40 EO | 0.95 | 0.95 | 0.95 |
| Ethanol | 10.0 | 10.0 | 10.0 |
| Polyglyceryl-4 Laurate/Sebacate (and) Polyglyceryl-6 Caprylate/Caprate (and) Aqua | — | 1.0 | — |
| Polyglyceryl-4 Laurate/Sebacate (and) Polyglyceryl-4 Caprylate/Caprate (and) Aqua | — | — | 1.5 |
| Water, perfume, preservative | to 100 | to 100 | to 100 |
| Turbidity value | 93.1% | 100.7% | 99.9% |

The comparison formulation V1 is, as compared with the formulations according to the present invention, diffuse and not unequivocally clear. Only the compositions according to the present invention are so.

The pH values of all formulations were adjusted to 2.5 to 3.0. All formulations were stable in a storage test at −8° C., 5° C., 23° C., and 40° C.

Of the 10 test subjects, all rated the formulations as good immediately after application. After one hour, only the compositions according to the present invention were rated as good. Eight test subjects perceived only a slight itching of the scalp in the case of the comparison formulation. One subject complained of severe itching of the scalp. The compositions according to the present invention are thus rated appreciably better than the comparison formulation.

Care-providing spray, also usable in foam form and/or as a hair treatment:

|  | K1 | K2 | K3 | K4 | K5 | K6 | K7 | K8 | K9 | K10 | K11 |
| --- | --- | --- | --- | --- | --- | --- | --- | --- | --- | --- | --- |
| Polymer JR 400 | 0.2 | 0.2 | 0.2 | 0.2 | 0.2 | 0.2 | 0.2 | 0.2 | 0.2 | 0.2 | 0.2 |
| Amocare VGH 70 | 0.5 | 0.5 | 0.5 | 0.5 | 0.5 | 0.5 | 0.5 | 0.5 | 0.5 | 0.5 | 0.5 |
| Stearamidopropyl-dimethylamine | 0.5 | 0.5 | 0.5 | 0.5 | 0.5 | 0.5 | 0.5 | 0.5 | 0.5 | 0.5 | 0.5 |
| PVP/VA Copolymer 60/40 | 1.0 | 1.0 | 1.0 | 1.0 | 1.0 | 1.0 | 1.0 | 1.0 | 1.0 | 1.0 | 1.0 |
| Polyquaternium-77 | 0.5 | — | — | — | — | — | 0.5 | — | — | — | 0.5 |
| Polyquaternium-78 | — | 0.5 | — | — | — | — | — | 0.5 | — | — | — |
| Polyquaternium-79 | — | — | 0.5 | — | — | — | — | — | 0.5 | 0.5 | — |
| Polyquaternium-80 | — | — | — | 0.5 | — | — | 0.5 | — | — | 0.5 | — |
| Polyquaternium-81 | — | — | — | — | 0.5 | — | — | 0.5 | — | — | 0.5 |
| Polyquaternium-82 | — | — | — | — | — | 0.5 | — | 0.5 | — | — | — |
| Panthenol | 0.2 | 0.2 | 0.2 | 0.2 | 0.2 | 0.2 | 0.2 | 0.2 | 0.2 | 0.2 | 0.2 |
| Cetrimonium chloride | 5.0 | 5.0 | 5.0 | 5.0 | 5.0 | 5.0 | 5.0 | 5.0 | 5.0 | 5.0 | 5.0 |
| Polyglyceryl-4 Laurate/Sebacate (and) Polyglyceryl-6 Caprylate/Caprate (and) Aqua | 1.5 | 1.5 | 1.5 | 1.5 | 1.5 | 1.5 | 1.5 | 1.5 | 1.5 | 1.5 | 1.5 |
| Protein hydrolysate | 0.2 | 0.2 | 0.2 | 0.2 | 0.2 | 0.2 | 0.2 | 0.2 | 0.2 | 0.2 | 0.2 |
| Dow Corning 193 | 0.2 | 0.2 | 0.2 | 0.2 | 0.2 | 0.2 | 0.2 | 0.2 | 0.2 | 0.2 | 0.2 |
| Coco Betaine | 0.5 | 0.5 | 0.5 | 0.5 | 0.5 | 0.5 | 0.5 | 0.5 | 0.5 | 0.5 | 0.5 |
| Water, preservative, and optionally perfume oils | to 100 | to 100 | to 100 | to 100 | to 100 | to 100 | to 100 | to 100 | to 100 | to 100 | to 100 |

The pH values of all formulations were adjusted to 2 to 6.

For application as a foam, the relevant formulation is either introduced along with a propellant gas into an aerosol container, or discharged as a foam from a pump bottle using a corresponding pump attachment, for example an air foamer.

For application as a hair treatment or cream, fatty alcohol such as cetylstearyl alcohol and/or ethylene glycol stearate and/or glycerol monostearate is added, in quantities from 0.2 to 5.0 wt %, to the formulations listed above.

Shampoo:

|  | S1 | S2 | S3 | S4 | S5 | S6 | S7 | S8 | S9 | S10 | S11 |
| --- | --- | --- | --- | --- | --- | --- | --- | --- | --- | --- | --- |
| Texapon ® N70 | 15.0 | 15.0 | 15.0 | 15.0 | 15.0 | 15.0 | 15.0 | 15.0 | 15.0 | 15.0 | 15.0 |
| Arlypon ® F | 0.15 | 0.15 | 0.15 | 0.15 | 0.15 | 0.15 | 0.15 | 0.15 | 0.15 | 0.15 | 0.15 |
| Antil ® 141 | 0.15 | 0.15 | 0.15 | 0.15 | 0.15 | 0.15 | 0.15 | 0.15 | 0.15 | 0.15 | 0.15 |
| Disodium Cocoampho-diacetate | 6.0 | 6.0 | 6.0 | 6.0 | 6.0 | 6.0 | 6.0 | 6.0 | 6.0 | 6.0 | 6.0 |
| Polyquaternium-77 | 0.5 | — | — | — | — | — | 0.5 | — | — | — | 0.5 |
| Polyquaternium-78 | — | 0.5 | — | — | — | — | — | 0.5 | — | — | — |
| Polyquaternium-79 | — | — | 0.5 | — | — | — | — | — | 0.5 | 0.5 | — |
| Polyquaternium-80 | — | — | — | 0.5 | — | — | 0.5 | — | — | 0.5 | — |
| Polyquaternium-81 | — | — | — | — | 0.5 | — | — | 0.5 | — | — | 0.5 |

-continued

|  | S1 | S2 | S3 | S4 | S5 | S6 | S7 | S8 | S9 | S10 | S11 |
|---|---|---|---|---|---|---|---|---|---|---|---|
| Polyquaternium-82 | — | — | — | — | — | 0.5 | — | — | 0.5 | — | — |
| Cetiol ® HE | 3.0 | 3.0 | 3.0 | 3.0 | 3.0 | 3.0 | 3.0 | 3.0 | 3.0 | 3.0 | 3.0 |
| Panthenol | 0.2 | 0.2 | 0.2 | 0.2 | 0.2 | 0.2 | 0.2 | 0.2 | 0.2 | 0.2 | 0.2 |
| Dow Corning 193 | 0.1 | 0.1 | 0.1 | 0.1 | 0.1 | 0.1 | 0.1 | 0.1 | 0.1 | 0.1 | 0.1 |
| Protein hydrolysate | 0.5 | 0.5 | 0.5 | 0.5 | 0.5 | 0.5 | 0.5 | 0.5 | 0.5 | 0.5 | 0.5 |
| Polyglyceryl-4 Laurate/Sebacate (and) Polyglyceryl-6 Caprylate/Caprate (and) Aqua | 1.5 | 1.5 | 1.5 | 1.5 | 1.5 | 1.5 | 1.5 | 1.5 | 1.5 | 1.5 | 1.5 |
| Water, preservative, and optionally perfume oils | to 100 | to 100 | to 100 | to 100 | to 100 | to 100 | to 100 | to 100 | to 100 | to 100 | to 100 |

The pH values of all formulations were adjusted to 4.5 to 5.8.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair treatment agent comprising, in combination with a cosmetic carrier, based in each case on the total composition:
   a) at least one cationic alkyloligoglucoside in a total quantity from 0.01 to 10.0 wt %, having the formula

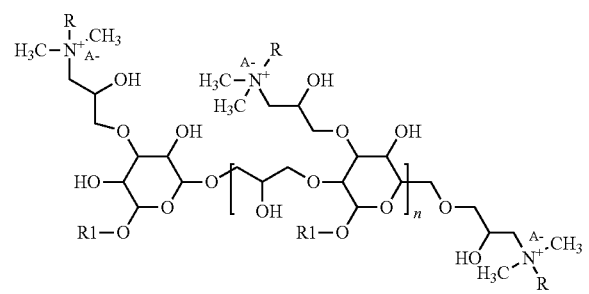

wherein residues R mutually independently denote a linear or branched C6 to C30 alkyl or alkenyl residue, and residues R1 mutually independently denote a linear or branched C6 to C30 alkyl or alkenyl residue, and
   b) at least one polyglycerol ester, in a total quantity from 0.01 to 10.0 wt %, the polyglycerol esters being esters of a fatty acid having 4 to 30 carbon atoms and polyglycerol having 2 to 20 glycerol units; and wherein $A^-$ denotes a physiologically acceptable anion.

2. The hair treatment agent according to claim 1, further comprising at least one quaternary ammonium compound, in a total quantity of from 0.1 to 10.0 wt %, selected from one of the groups of
   esterquats;
   quaternary imidazolines of formula I,

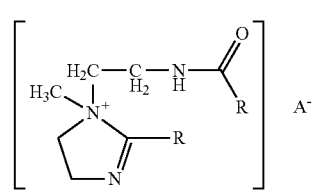

formula I in which residues R, mutually independently in each case, denote a saturated or unsaturated, linear or branched hydrocarbon residue having a chain length from 8 to 30 carbon atoms, and $A^-$ denotes a physiologically acceptable anion;
   cetrimonium chloride and/or behentrimonium chloride;
   cationized amines;
   poly(methacryloyloxyethyltrimethylammonium) compounds; and/or
   quaternized cellulose derivatives selected from the group consisting of Polyquaternium-10, Polyquaternium-24, Polyquaternium-67, and Polyquaternium-72;
   cationized honey;
   polymeric dimethyldiallylammonium salts and copolymers thereof with esters and amides of acrylic acid and methacrylic acid;
   copolymers of vinylpyrrolidone with quaternized derivatives of dialkylaminoalkyl acrylate and methacrylate;
   vinylpyrrolidone-vinylimidazolium methochloride copolymers;
   quaternized polyvinyl alcohol;
   Polyquaternium-2;
   Polyquaternium-7;
   Polyquaternium-16;
   Polyquaternium-17;
   Polyquaternium-18;
   Polyquaternium-27;
   Polyquaternium-69; and
   Polyquaternium-74.

3. The hair treatment agent according to claim 2, wherein the quaternary ammonium compound is selected from at least one of the groups of cationic surfactants or any mixtures thereof, in a total quantity from 0.01 to 10.0 wt %, the cationic surfactants being selected from at least one of the groups of
   i) esterquats;
   ii) quaternary imidazolines of formula (Tkat2),

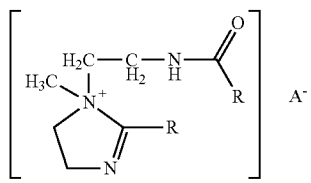

wherein residues R, mutually independently in each case, denote a saturated or unsaturated, linear or branched hydrocarbon residue having a chain length from 8 to 30 carbon atoms, and $A^-$ denotes a physiologically acceptable anion;

iii) cetrimonium chloride and/or behentrimonium chloride; and iv) cationized amines.

4. The hair treatment agent according to claim 3, wherein the cationic surfactant is selected from the group consisting of stearamidopropyldimethylamine, distearoylethyl hydroxyethylmonium methosulfate, dicocoyl hydroxyethylmonium methosulfate, dipalmitoylethyl dimonium chloride, Quaternium-27, Quaternium-91, and behenoyl PG-trimonium Chloride.

5. The hair treatment agent according to claim 1, further comprising a surfactant selected from zwitterionic and amphoteric surfactants, in a total quantity from 0.01 to 5.0 wt %.

6. The hair treatment agent according to claim 5, wherein the zwitterionic and/or amphoteric surfactant is selected from cocamidopropyl betaine, coco betaine, and mixtures thereof.

7. The hair treatment agent according to claim 1, further comprising fatty alcohols having a number of carbons from 10 to 30 at a concentration that is less than 2.0 wt %.

8. The hair treatment agent according to claim 1, wherein no silicone is included in the hair treatment.

9. The hair treatment agent according to claim 1, further comprising at least one active substance selected from the group constituted by carnitine, taurine, coenzyme Q-10, ectoin, purine, adenine, guanine, uric acid, hypoxanthine, 6-purinethiol, 6-thioguanine, xanthine, caffeine, theobromine, theophylline, and a vitamin of the B series.

10. The hair treatment agent according to claim 1, wherein the at least one cationic alkyloligoglucoside is selected from the group consisting of Polyquaternium-77, Polyquaternium-78, Polyquaternium-79, Polyquaternium-80, Polyquaternium-81, and Polyquaternium-82.

11. The hair treatment agent according to claim 1, wherein the at least one polyglycerol ester is selected from the group consisting of Polyglyceryl-4 Caprate, Polyglyceryl-2 Caprate, Polyglyceryl-4 Caprylate, Polyglyceryl-6 Caprylate, Polyglyceryl-6 Caprate, Polyglyceryl-4 Caprylate/Caprate, Polyglyceryl-6 Caprylate/Caprate, Polyglyceryl-3 Cocoate, Polyglyceryl-4 Cocoate, Polyglyceryl-10 Decalinoleate, Polyglyceryl-10 Decaoleate, Polyglyceryl-10 Decacasterate, Polyglyceryl-3 Dicaprate, Polyglyceryl-3 Dicocoate, Polyglyceryl-10 Didecanoate, Polyglyceryl-2 Diisostearate, Polyglyceryl-3 Diisostearate, Polyglyceryl-10 Diisostearate, Polyglyceryl-4 Dilaurate, Polyglycerin-2 Dioleate, Polyglyceryl-3 Dioleate, Polyglyceryl-6 Dioleate, Polyglyceryl-10 Dioleate, Polyglyceryl-6 Dipalmitate, Polyglyceryl-10 Dipalmitate, Polyglyceryl-2 Dipolyhydroxystearate, Polyglyceryl-2 Distearate, Polyglyceryl-3 Distearate, Polyglyceryl-6 Distearate, Polyglyceryl-10 Distearate, Polyglyceryl-10 Heptaoleate, Polyglyceryl-10 Heptastearate, Polyglyceryl-6 Hexaoleate, Polyglyceryl-10 Hexaoleate, Polyglyceryl-2 Isopalmitate, Polyglyceryl-2 Isostearate, Polyglyceryl-4 Isostearate, Polyglyceryl-5 Isostearate, Polyglyceryl-6 Isostearate, Polyglyceryl-10 Isostearate, Polyglyceryl-2 Laurate, Polyglyceryl-3 Laurate, Polyglyceryl-4 Laurate, Polyglyceryl-4 Laurate/Sebacate, Polyglyceryl-4 Laurate/Succinate, Polyglyceryl-5 Laurate, Polyglyceryl-6 Laurate, Polyglyceryl-10 Laurate, Polyglyceryl-3 Myristate, Polyglyceryl-10 Myristate, Polyglyceryl-2 Oleate, Polyglyceryl-3 Oleate, Polyglyceryl-4 Oleate, Polyglyceryl-5 Oleate, Polyglyceryl-6 Oleate, Polyglyceryl-8 Oleate, Polyglyceryl-10 Oleate, Polyglyceryl-3 Palmitate, Polyglyceryl-6 Palmitate, Polyglyceryl-10 Pentalaurate, Polyglyceryl-10 Pentalinoleate, Polyglyceryl-4 Pentaoleate, Polyglyceryl-10 Pentaoleate, Polyglyceryl-3 Pentaricinoleate, Polyglyceryl-6 Pentaricinoleate, Polyglyceryl-10 Pentaricinoleate, Polyglyceryl-4 Pentastearate, Polyglyceryl-6 Pentastearate, Polyglyceryl-10 Pentastearate, Polyglyceryl-3 Polyrisinoleate, Polyglyceryl-6 Polyricinoleate, Polyglyceryl-3 Ricinoleate, Polyglyceryl-2 Sesquiisostearate, Polyglyceryl-2 Sesquioleate, Polyglyceryl-2 Sesquistearate, Polyglyceryl-3 Stearate, Polyglyceryl-2 Stearate, Polyglyceryl-4 Stearate, Polyglyceryl-8 Stearate, Polyglyceryl-10 Stearate, Polyglyceryl-2 Tetraisostearate, Polyglyceryl-6 Tetraoleate, Polyglyceryl-10 Tetraoleate, Polyglyceryl-2 Tetrastearate, Polyglyceryl-2 Triisostearate, Polyglyceryl-3 Triisostearate, Polyglyceryl-10 Trioleate, Polyglyceryl-4 Tristearate, Polyglyceryl Tristearate, and Polyglyceryl-10 Tristearate.

12. A method for treating keratinic fibers, comprising:
applying the cosmetic composition according to claim 1 onto the keratinic fibers and allowing the cosmetic composition to remain, without being rinsed out, until the hair is next washed.

* * * * *